(12) United States Patent
Becerra et al.

(10) Patent No.: US 11,627,867 B2
(45) Date of Patent: Apr. 18, 2023

(54) SURGICAL ROBOTIC ACCESS SYSTEM FOR IRREGULARLY SHAPED ROBOTIC ACTUATORS AND ASSOCIATED ROBOTIC SURGICAL INSTRUMENTS

(71) Applicant: Applied Medical Resources Corporation, Rancho Santa Margarita, CA (US)

(72) Inventors: Matthew Becerra, Lake Forest, CA (US); Jeremy Albrecht, Rancho Santa Margarita, CA (US); Timothy Hopkins, Rancho Santa Margarita, CA (US); Brian Pugh, Lake Forest, CA (US); Brian Hong, Sunnyvale, CA (US); Bruno Vu, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 351 days.

(21) Appl. No.: 16/896,688

(22) Filed: Jun. 9, 2020

(65) Prior Publication Data
US 2020/0297196 A1   Sep. 24, 2020

Related U.S. Application Data

(63) Continuation of application No. 15/697,288, filed on Sep. 6, 2017, now Pat. No. 10,674,896.
(Continued)

(51) Int. Cl.
*A61B 1/00* (2006.01)
*A61B 17/34* (2006.01)
(Continued)

(52) U.S. Cl.
CPC ........ *A61B 1/00154* (2013.01); *A61B 1/0055* (2013.01); *A61B 17/3423* (2013.01);
(Continued)

(58) Field of Classification Search
CPC .. A61B 1/00154; A61B 90/50; A61B 17/3468
See application file for complete search history.

(56) References Cited

U.S. PATENT DOCUMENTS

| 558,364 A | 4/1896 | Doolittle |
| 958,854 A | 5/1910 | Bunn |

(Continued)

FOREIGN PATENT DOCUMENTS

| DE | 26 05 148 A1 | 8/1977 |
| DE | 33 36 279 A1 | 1/1986 |

(Continued)

OTHER PUBLICATIONS

European Patent Office, the International Search Report and Written Opinion of the International Searching Authority for International Application No. PCT/US2016/049740 titled "Surgical Robotic Access System", dated Nov. 21, 2016, 11 pgs.
(Continued)

*Primary Examiner* — Nicholas W Woodall
(74) *Attorney, Agent, or Firm* — Thomas Nguyen; Patrick Ikehara

(57) ABSTRACT

The surgical robotic access system provides access for robotic instruments and/or actuators including the introduction, operation and withdrawal of such robotic manipulators into a body cavity without permitting the escape of pressurized fluid or gas. The surgical robotic access system also provides a multi-faceted range of movement without touching or effecting pressure on the opening in the patient's body cavity.

20 Claims, 29 Drawing Sheets

Related U.S. Application Data

(60) Provisional application No. 62/393,305, filed on Sep. 12, 2016.

(51) Int. Cl.
  *A61B 90/50* (2016.01)
  *A61B 34/30* (2016.01)
  *A61B 1/005* (2006.01)
  *A61B 90/00* (2016.01)
  *A61B 17/00* (2006.01)

(52) U.S. Cl.
  CPC ...... *A61B 17/3496* (2013.01); *A61B 17/3498* (2013.01); *A61B 34/30* (2016.02); *A61B 90/50* (2016.02); *A61B 2017/00477* (2013.01); *A61B 2017/346* (2013.01); *A61B 2017/3419* (2013.01); *A61B 2090/0801* (2016.02)

(56) References Cited

U.S. PATENT DOCUMENTS

| | | |
|---|---|---|
| 1,157,202 A | 10/1915 | Bates et al. |
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 2,907,321 A | 10/1959 | Rubens |
| 3,039,468 A | 6/1962 | Price |
| 3,057,350 A | 10/1962 | Cowley |
| 3,111,943 A | 11/1963 | Orndorff |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,729,027 A | 4/1973 | Bare |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazal Is |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,082,005 A | 4/1978 | Erdley |
| 4,083,370 A | 4/1978 | Taylor |
| 4,096,853 A | 6/1978 | Weigand |
| 4,112,932 A | 9/1978 | Chiulli |
| 4,117,847 A | 10/1978 | Clayton |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Banjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |

(56) References Cited

U.S. PATENT DOCUMENTS

| | | |
|---|---|---|
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,144,942 A | 9/1992 | Decarie et al. |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Rirchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III et al. |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Durdal et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |

(56) References Cited

U.S. PATENT DOCUMENTS

| | | |
|---|---|---|
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins, III et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Strouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchiffe et al. |
| 5,957,913 A | 9/1999 | de la Torre et al. |
| 5,962,572 A | 10/1999 | Chen |
| 5,964,781 A | 10/1999 | Mollenauer et al. |
| 5,976,174 A | 11/1999 | Ruiz |
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,994,450 A | 11/1999 | Pearce |
| 5,997,515 A | 12/1999 | de la Torre et al. |
| 6,004,303 A | 12/1999 | Peterson |
| 6,007,544 A | 12/1999 | Kim |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |
| 6,050,871 A | 4/2000 | Chen |
| 6,053,934 A | 4/2000 | Andrews et al. |
| 6,059,816 A | 5/2000 | Moenning |
| 6,066,117 A | 5/2000 | Fox et al. |
| 6,068,639 A | 5/2000 | Fogarty et al. |
| 6,076,560 A | 6/2000 | Stahle et al. |
| 6,077,288 A | 6/2000 | Shimomura |
| 6,086,603 A | 7/2000 | Termin et al. |

(56) References Cited

U.S. PATENT DOCUMENTS

| | | |
|---|---|---|
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,041,056 B2 | 5/2006 | Deslauriers et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Liu et al. |
| 7,105,009 B2 | 9/2006 | Johnson |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |

(56) References Cited

U.S. PATENT DOCUMENTS

| | | |
|---|---|---|
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,546 B2 | 3/2008 | Wulfman et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,678,046 B2 | 3/2010 | White et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,822 B2 | 8/2010 | White et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,841,765 B2 | 11/2010 | Keller |
| 7,850,667 B2 | 12/2010 | Gresham |
| 7,867,164 B2 | 1/2011 | Butler et al. |
| 7,878,974 B2 | 2/2011 | Brustad et al. |
| 7,896,889 B2 | 3/2011 | Mazzocchi et al. |
| 7,909,760 B2 | 3/2011 | Albrecht et al. |
| 7,930,782 B2 | 4/2011 | Chen |
| RE42,379 E | 5/2011 | Loomas |
| 7,951,076 B2 | 5/2011 | Hart et al. |
| 7,998,068 B2 | 8/2011 | Bonadio et al. |
| 8,016,755 B2 | 9/2011 | Ewers et al. |
| 8,021,296 B2 | 9/2011 | Bonadio et al. |
| 8,070,676 B2 | 12/2011 | Ewers et al. |
| 8,105,234 B2 | 1/2012 | Ewers et al. |
| 8,109,873 B2 | 2/2012 | Albrecht et al. |
| 8,142,354 B1 | 3/2012 | Larson et al. |
| 8,187,177 B2 | 5/2012 | Kahle et al. |
| 8,226,552 B2 | 7/2012 | Albrecht et al. |
| 8,235,054 B2 | 8/2012 | Nguyen et al. |
| 8,262,568 B2 | 9/2012 | Albrecht et al. |
| 8,262,622 B2 | 9/2012 | Gonzales et al. |
| 8,267,858 B2 | 9/2012 | Albrecht et al. |
| 8,308,639 B2 | 11/2012 | Albrecht et al. |
| 8,313,431 B2 | 11/2012 | Albrecht et al. |
| 8,317,690 B2 | 11/2012 | Ransden et al. |
| 8,343,047 B2 | 1/2013 | Albrecht et al. |
| 8,388,526 B2 | 3/2013 | Ewers et al. |
| 8,414,487 B2 | 4/2013 | Albrecht et al. |
| RE44,380 E | 7/2013 | de la Torre et al. |
| 8,574,153 B2 | 11/2013 | Shelton |
| 8,647,265 B2 | 2/2014 | Brustad et al. |
| RE44,790 E | 3/2014 | de la Torre et al. |
| 9,615,908 B2 * | 4/2017 | Anderson ............ A61F 2/0095 |
| 9,808,284 B2 * | 11/2017 | Anderson ............ A61B 17/02 |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0049276 A1 | 4/2002 | Zwick |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0014076 A1 | 1/2003 | Mollenauer et al. |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0082969 A1 | 4/2004 | Kerr |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0230218 A1 | 11/2004 | Criscuolo et al. |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0260246 A1 | 12/2004 | Desmond |
| 2004/0267096 A1 | 12/2004 | Caldwell et al. |
| 2005/0015103 A1 | 1/2005 | Popov |
| 2005/0020884 A1 | 1/2005 | Hart et al. |
| 2005/0033246 A1 | 2/2005 | Ahlbert et al. |
| 2005/0049624 A1 | 3/2005 | Francese et al. |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkier, II et al. |
| 2005/0090713 A1 | 4/2005 | Gozales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |

(56) References Cited

U.S. PATENT DOCUMENTS

| | | |
|---|---|---|
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0200186 A1 | 9/2006 | Marchek et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1* | 11/2006 | Piskun ............ A61B 17/320016 600/105 |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0088204 A1 | 4/2007 | Albrecht |
| 2007/0088241 A1 | 4/2007 | Brustad et al. |
| 2007/0093695 A1 | 4/2007 | Bonadio et al. |
| 2007/0118175 A1 | 5/2007 | Butler et al. |
| 2007/0135679 A1 | 6/2007 | Hunt et al. |
| 2007/0149859 A1 | 6/2007 | Albrecht |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0198059 A1* | 8/2007 | Patel ...................... A61B 50/30 606/213 |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270752 A1 | 11/2007 | Labombard |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0030375 A1 | 1/2009 | Franer et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0182282 A1 | 7/2009 | Okihisa |
| 2009/0187079 A1 | 7/2009 | Albrecht et al. |
| 2009/0227843 A1 | 9/2009 | Smith et al. |
| 2009/0234380 A1* | 9/2009 | Gabel ............... A61M 37/0069 606/198 |
| 2009/0281500 A1 | 11/2009 | Acosta et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0094227 A1 | 4/2010 | Albrecht et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegel et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2011/0021877 A1 | 1/2011 | Fortier et al. |
| 2011/0028891 A1 | 2/2011 | Okoniewski |
| 2011/0034935 A1 | 2/2011 | Kleyman |
| 2011/0034946 A1 | 2/2011 | Kleyman |
| 2011/0034947 A1 | 2/2011 | Kleyman |
| 2011/0071462 A1 | 3/2011 | Ewers et al. |
| 2011/0071463 A1 | 3/2011 | Ewers et al. |
| 2011/0071542 A1 | 3/2011 | Prisco et al. |
| 2011/0251466 A1 | 10/2011 | Kleyman et al. |
| 2011/0277775 A1 | 11/2011 | Holop et al. |
| 2012/0095297 A1 | 4/2012 | Dang et al. |
| 2012/0296151 A1 | 11/2012 | Curtis et al. |
| 2013/0053779 A1 | 2/2013 | Shelton, IV |
| 2014/0039268 A1 | 2/2014 | Richard |
| 2014/0163326 A1 | 6/2014 | Forsell |
| 2014/0276437 A1 | 9/2014 | Hart et al. |
| 2015/0126812 A1* | 5/2015 | Anderson ................ A61F 2/12 600/203 |

FOREIGN PATENT DOCUMENTS

| | | |
|---|---|---|
| DE | 37 39 532 C1 | 12/1988 |
| DE | 37 37 121 A1 | 5/1989 |
| DE | 296 00 939 U1 | 5/1996 |
| DE | 19828099 A1 | 12/1999 |
| EP | 0 113 520 A2 | 7/1984 |
| EP | 0 142 262 A1 | 5/1985 |
| EP | 0 487 175 A1 | 5/1992 |
| EP | 0 517 248 A1 | 12/1992 |
| EP | 0 537 768 A1 | 4/1993 |
| EP | 0 542 428 A1 | 5/1993 |
| EP | 0 807 416 A2 | 11/1997 |
| EP | 0 849 517 B1 | 6/1998 |
| EP | 0 950 376 B1 | 10/1999 |
| EP | 0 980 677 A1 | 2/2000 |
| EP | 1 118 657 A1 | 7/2001 |
| EP | 1 125 552 A1 | 8/2001 |
| EP | 1 312 318 B1 | 5/2003 |
| EP | 1 407 715 A1 | 4/2004 |
| EP | 1 852 053 A1 | 11/2007 |
| EP | 1 940 282 B1 | 7/2008 |
| EP | 1 948 047 B1 | 7/2008 |
| EP | 2 044 889 A1 | 4/2009 |
| EP | 2 272 449 A2 | 1/2011 |
| EP | 2 272 450 A3 | 1/2011 |
| EP | 2 340 792 A1 | 7/2011 |
| FR | 1456623 A | 7/1966 |
| GB | 1151993 A | 5/1969 |
| GB | 1355611 A | 6/1974 |
| GB | 1372491 A | 10/1974 |

(56) References Cited

FOREIGN PATENT DOCUMENTS

| | | |
|---|---|---|
| GB | 1379772 A | 1/1975 |
| GB | 1400808 A | 7/1975 |
| GB | 1407023 A | 9/1975 |
| GB | 1482857 A | 8/1977 |
| GB | 1496696 A | 12/1977 |
| GB | 2071502 A | 9/1981 |
| GB | 2255019 A | 10/1992 |
| GB | 2275420 A | 8/1994 |
| GB | 2298906 A | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S71634 | 2/1997 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 A | 4/1998 |
| JP | 11-290327 A | 10/1999 |
| JP | 2001-61850 A | 3/2001 |
| JP | 2002-28163 A | 1/2002 |
| JP | 2003 235879 A | 8/2003 |
| JP | 2004-195037 A | 7/2004 |
| SU | 1342485 A1 | 10/1987 |
| WO | WO 86/06272 A1 | 11/1986 |
| WO | WO 86/06316 A1 | 11/1986 |
| WO | WO 92/11880 A1 | 7/1992 |
| WO | WO 92/21292 A2 | 12/1992 |
| WO | WO 93/05740 A1 | 4/1993 |
| WO | WO 93/14801 A1 | 8/1993 |
| WO | WO 94/04067 A1 | 3/1994 |
| WO | WO 94/22357 A2 | 10/1994 |
| WO | WO 95/05207 A2 | 2/1995 |
| WO | WO 95/07056 A2 | 3/1995 |
| WO | WO 95/22289 A2 | 8/1995 |
| WO | WO 95/24864 A1 | 9/1995 |
| WO | WO 95/27445 A1 | 10/1995 |
| WO | WO 95/27468 A1 | 10/1995 |
| WO | WO 96/23536 A1 | 8/1996 |
| WO | WO 96/36283 A1 | 11/1996 |
| WO | WO 97/11642 A1 | 4/1997 |
| WO | WO 97/32514 A2 | 9/1997 |
| WO | WO 97/32515 A1 | 9/1997 |
| WO | WO 97/42889 A1 | 11/1997 |
| WO | WO 98/19853 A1 | 5/1998 |
| WO | WO 98/35614 A1 | 8/1998 |
| WO | WO 98/48724 A1 | 11/1998 |
| WO | WO 99/03416 A1 | 1/1999 |
| WO | WO 99/15068 A2 | 4/1999 |
| WO | WO 99/16368 A1 | 4/1999 |
| WO | WO 99/22804 A1 | 5/1999 |
| WO | WO 99/25268 A1 | 5/1999 |
| WO | WO 99/29250 A1 | 6/1999 |
| WO | WO 00/32116 A1 | 6/2000 |
| WO | WO 00/32117 A1 | 6/2000 |
| WO | WO 00/32119 A1 | 6/2000 |
| WO | WO 00/32120 A1 | 6/2000 |
| WO | WO 00/35356 A1 | 6/2000 |
| WO | WO 00/54675 A1 | 9/2000 |
| WO | WO 00/54676 A1 | 9/2000 |
| WO | WO 00/54677 A1 | 9/2000 |
| WO | WO 01/08563 A2 | 2/2001 |
| WO | WO 01/08581 A2 | 2/2001 |
| WO | WO 01/26558 A1 | 4/2001 |
| WO | WO 01/26559 A1 | 4/2001 |
| WO | WO 01/45568 A1 | 6/2001 |
| WO | WO 01/49363 A1 | 7/2001 |
| WO | WO 01/91652 A1 | 12/2001 |
| WO | WO 02/07611 A2 | 1/2002 |
| WO | WO 02/17800 A2 | 3/2002 |
| WO | WO 02/34108 A2 | 5/2002 |
| WO | WO 03/011153 A1 | 2/2003 |
| WO | WO 03/011551 A1 | 2/2003 |
| WO | WO 03/026512 A1 | 4/2003 |
| WO | WO 03/032819 A1 | 4/2003 |
| WO | WO 03/034908 A2 | 5/2003 |
| WO | WO 03/061480 A1 | 7/2003 |
| WO | WO 03/077726 A2 | 9/2003 |
| WO | WO 03/103548 A1 | 12/2003 |
| WO | WO 2004/026153 A1 | 4/2004 |
| WO | WO 2004/030547 A1 | 4/2004 |
| WO | WO 2004/075730 A2 | 9/2004 |
| WO | WO 2004/075741 A2 | 9/2004 |
| WO | WO 2004/075930 A2 | 9/2004 |
| WO | WO 2005/009257 A2 | 2/2005 |
| WO | WO 2005/013803 A2 | 2/2005 |
| WO | WO 2005/034766 A2 | 4/2005 |
| WO | WO 2005/089661 A1 | 9/2005 |
| WO | WO 2006/040748 A1 | 4/2006 |
| WO | WO 2006/059318 A1 | 6/2006 |
| WO | WO 2006/100658 A2 | 9/2006 |
| WO | WO 2007/044849 A1 | 4/2007 |
| WO | WO 2007/109700 A2 | 9/2007 |
| WO | WO 2008/015566 A2 | 2/2008 |
| WO | WO 2008/093313 A1 | 8/2008 |
| WO | WO 2008/121294 A1 | 10/2008 |
| WO | WO 2010/045253 A1 | 4/2010 |
| WO | WO 2010/082722 A1 | 7/2010 |
| WO | WO 2010/104259 A1 | 9/2010 |
| WO | WO 2015/063497 A1 | 5/2015 |

OTHER PUBLICATIONS

The International Searching Authority, the International Search Report and Written Opinion of the International Searching Authority for International Application No. PCT/US2017/050340, entitled "Surgical Robotic Access System for Irregularly Shaped Robotic Actuators and Associated Robotic Surgical Instruments," dated Feb. 2, 2018, 30 pgs.

The International Bureau of WIPO, International Preliminary Report on Patentability for International Application No. PCT/US2017/050340, entitled "Surgical Robotic Access System for Irregularly Shaped Robotic Actuators and Associated Robotic Surgical Instruments," dated Mar. 21, 2019, 20 pgs.

U.S. Appl. No. 10/902,756, filed Jul. 29, 2004; Title: Hand Access Port Device, now abandoned.

U.S. Appl. No. 10/802,125, filed Mar. 15, 2004; Title: Surgical Guide Valve, now abandoned.

U.S. Appl. No. 10/927,551, filed Aug. 25, 2004; Title: Surgical Access System, now abandoned.

U.S. Appl. No. 11/330,661, filed Jan. 12, 2006; Title: Sealed Surgical Access Device, Hart et al., now abandoned.

U.S. Appl. No. 12/360,634, filed Jan. 27, 2009; Title: Surgical Access Apparatus and Method, now abandoned.

U.S. Appl. No. 12/004,439, filed Dec. 20, 2007; Title: Skin Seal, now abandoned.

U.S. Appl. No. 12/004,441, filed Dec. 20, 2007; Title: Screw-Type Skin Seal With Inflatable Membrane, now abandoned.

U.S. Appl. No. 10/965,217, filed Oct. 15, 2004; Title: Surgical Sealing Device, now abandoned.

U.S. Appl. No. 10/981,730, filed Nov. 5, 2004; Title: Surgical Sealing Device, now abandoned.

U.S. Appl. No. 11/291,089, filed Dec. 1, 2005; Title: a Surgical Sealing Device, now abandoned.

U.S. Appl. No. 11/785,752, filed Apr. 19, 2007; Title: Instrument Access Device, now abandoned.

U.S. Appl. No. 12/244,024, filed Oct. 2, 2008; Title: Seal Anchor for Use in Surgical Procedures, now abandoned.

U.S. Appl. No. 12/578,832, filed Oct. 14, 2009; Title: Flexible Access Device for Use in Surgical Procedure, now abandoned.

(56) References Cited

OTHER PUBLICATIONS

U.S. Appl. No. 10/913,565, filed Aug. 5, 2004; Title: Surgical Device With Tack-Free Gel and Method of Manufacture, now abandoned.
Dexterity Protractor Instruction Manual by Dexterity Surgical, Inc., dated 1999, 8 pgs.
European Patent Office, European Search Report for European Application No. EP 10 18 4681, entitled "Wound Retraction Apparatus and Method," dated Nov. 22, 2010.
European Patent Office, European Search Report for European Application No. EP 10 18 4608, entitled "Wound Retraction Apparatus and Method," dated Nov. 22, 2010.
European Patent Office, European Search Report for European Application No. EP 10 18 4648, entitled "Wound Retraction Apparatus and Method", dated Nov. 22, 2010.
European Patent Office, European Search Report for European Application No. EP 10 18 4731, entitled "Wound Retraction Apparatus and Method", dated Nov. 22, 2010.
European Patent Office, European Search Report for European Application No. EP 10 18 4661, entitled "Wound Retraction Apparatus and Method", dated Nov. 22, 2010.
European Patent Office, European Search Report for European Application No. EP 10 18 4677, entitled "Wound Retraction Apparatus and Method," dated Nov. 22, 2010.
European Patent Office, European Search Report for European Application No. EP 10 18 9325, entitled "Split Hoop Wound Retractor", dated Dec. 14, 2010.
European Patent Office, European Search Report for European Application No. EP 10 18 9327, entitled "Split Hoop Wound Retractor", dated Dec. 14, 2010.
European Patent Office, European Search Report for European Application No. EP 10 18 9328, entitled "Split Hoop Wound Retractor", dated Dec. 15, 2010.
European Patent Office, European Search Report for European Application No. EP 04 00 2888, entitled "Hand Access Port Device", dated Sep. 10, 2004.
European Patent Office, European Search Report for European Application No. EP 04 00 2889, entitled "Hand Access Port Device", dated Sep. 13, 2004.
European Patent Office, International Search Report and the Written Opinion of the International Searching Authority for International Application No. PCT/US2006/040154, entitled, "Method of Making a Hand Access Laparoscopic Device," dated Jan. 30, 2007, 9 pgs.
European Patent Office, International Search Report and the Written Opinion of the International Searching Authority for International Application No. PCT/US2006/040073, entitled, "Split Hoop Wound Retractor," dated Jan. 26, 2007, 8 pgs.
European Patent Office, International Search Report and the Written Opinion of the International Searching Authority for International Application No. PCT/US2006/039905, entitled, "Wound Retractor with Gel Cap," dated Jan. 17, 2007, 8 pgs.
European Patent Office, International Search Report and the Written Opinion of the International Searching Authority for International Application No. PCT/US2006/039883, entitled, "Circular Surgical Retractor," dated Jan. 31, 2007, 8 pgs.
European Patent Office, International Search Report and the Written Opinion of the International Searching Authority for International Application No. PCT/US2006/039800, entitled, "Hand Access Laparoscopic Device," dated Apr. 16, 2007, 14 pgs.
European Patent Office, International Search Report and the Written Opinion of the International Searching Authority for International Application No. PCT/US2006/039799, entitled, "Split Hoop Wound Retractor with Gel Cap," dated Mar. 27, 2007, 11 pgs.
European Patent Office, European Search Report for European Application No. EP 08253236 dated Feb. 10, 2009, 6 pgs.
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484, entitled, "Sealed Surgical Access Device," dated Nov. 12, 2004, 9 pgs.
International Searching Authority/US, International Search Report and the Written Opinion of the International Searching Authority for International Application No. PCT/US01/29682, entitled, "Surgical Access Apparatus and Method," dated Jun. 14, 2002, 8 pgs.
McSweeney, Cannulation of the Rumen in Cattle and Buffaloes, Australian Veterinary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005, 16 pgs.
Office Action in co-pending U.S. Appl. No. 12/360,634, dated Jan. 24, 2011, 12 pages.
Office Action in co-pending U.S. Appl. No. 12/360,710, dated Jan. 24, 2011, 12 pages.
Technical Note: Development of Duodenal Cannula for Sheep, Faculty of Agriculture and School of Medicine Tohokju University, Sendai 981, Japan, dated 1992, 5 pgs.
The International Bureau of WIPO, International Preliminary Report on Patentability for International Application No. PCT/US2004/028250, entitled, "Surgical Instrument Access Device," dated Aug. 29, 2006, 8 pgs.
The International Bureau of WIPO, International Preliminary Report on Patentability for International Application No. PCT/US2006/039799, entitled, "Split Hoop Wound Restractor with Gel Pad," dated Apr. 16, 2008, 7 pgs.
The International Bureau of WIPO, International Preliminary Report on Patentability for International Application No. PCT/US2006/039800, "Hand Access Laparoscopic Device," dated Apr. 16, 2008, 9 pgs.
Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.
Kagaya, "Laparascopic cholecystecomy via two ports, using the Twin-Port" system, J. Hepatobiliary Pancreat Surg (2001) 8:76-80, dated Feb. 20, 2001.
Declaration of John R. Brustad dated Dec. 10, 2009, submitted in U.S. Appl. No. 11/548,955, including Appendices A-D regarding product sales brochures and production drawings from 2001 and 2005, 7 pgs.
International Search Report and Written Opinion for PCT/IE2005/000113, dated Feb. 22, 2006, 8 pgs.
International Searching Authority—US, International Search Report and Written Opinion of the International Searching Authority for International Application No. PCT/US04/25511, entitled, "Surgical Device with Tack-Free Gel and Method of Manufacture," dated Nov. 7, 2007, 12 pgs.
International Bureau of WIPO, International Report on Patentability for International Application No. PCT/US04/25511, entitled, "Surgical Device with Tack-Free Gel and Method of Manufacture," dated Dec. 6, 2007, 6 pgs.
International Search Report and Written Opinion for PCT/IE2007/000050 dated Aug. 13, 2007, 7 pgs.
The International Searching Authority, The International Search Report and Written Opinion of the International Searching Authority for International Application No. PCT/US08/63445, entitled, "Surgical retractor with Gel Pad," dated Sep. 29, 2008, 11 pgs.
The International Searching Authority, The International Search Report and Written Opinion of the International Searching Authority for International Application No. PCT/US08/063463, entitled, "Surgical Retractor," dated Sep. 10, 2008, 9 pgs.
The International Bureau of WIPO, International Preliminary Report on Patentability for International Application No. PCT/US2008/063463, entitled "Surgical Retractor", dated Nov. 17, 2009, 5 pgs.

(56) References Cited

OTHER PUBLICATIONS

The International Bureau of WIPO, International Preliminary Report on Patentability for International Application No. PCT/US08/63445, entitled "Surgical Retractor with Gel Pad", dated Nov. 17, 2009, 5 pgs.
International Searching Authority—European Patent Office, The International Search Report and Written Opinion for International Application No. PCT/US2009/060540, entitled, "Single Port Access System," dated Feb. 4, 2010, 17 pgs.
The International Bureau of WIPO, International Preliminary Report on Patentability for International Application No. PCT/US2009/060540, entitled, "Single Port Access System," dated Apr. 19, 2011, 8 pgs.
International Searching Authority—European Patent Office, The International Search Report and Written Opinion for International Application No. PCT/US2011/054266, entitled, "Natural Orifice Surgery System," dated Feb. 9, 2012, 13 pgs.
European Patent Office, European Search Report for European Patent No. 11172709.5, entitled, "Sealed Surgical Access Device," dated Aug. 16, 2011, 4 pgs.
European Patent Office, European Search Report for European Patent No. 11172706.1, entitled, "Sealed Surgical Access Device," dated Aug. 16, 2011, 3 pgs.
European Patent Office, European Search Report for European Patent No. 12151288, entitled, "Surgical Instrument Access Device," dated Feb. 10, 2012, 8 pgs.
European Patent Office, Supplementary European Search Report for European Patent Application No. 08755322, entitled, "Surgical Retractor with Gel Pad," dated Apr. 18, 2012, 3 pgs.
European Patent Office, Supplementary European Search Report for European Patent Application No. 08755336, entitled, "Surgical Retractor," dated Jun. 15, 2012, 2 pgs.
Harold W. Harrower, M.D., Isolation of Incisions into Body Cavities, The American Journal of Surgery, vol. 116, pp. 824-826, Dec. 1968.
International Searching Authority—European Patent Office, The International Search Report and Written Opinion for International Application No. PCT/US2013/037213, entitled, "Natural Orifice System," dated Jul. 3, 2013, 9 pgs.
International Searching Authority—European Patent Office, the International Search Report and Written Opinion for International Application No. PCT/US2012/060997, entitled, "Simulated Tissue Structure for Surgical Training," dated Mar. 7, 2013, 8 pgs.
The International Bureau of WIPO, International Preliminary Report on Patentability for International Application No. PCT/US2011/054266, entitled, "Natural Orifice Surgery System" dated Apr. 2, 2013, 8 pgs.
European Patent Office, International Search Report and Written Opinion for International Application No. PCT/US2014/027258, titled Mechanical Gel Surgical Access Device, dated Jun. 3, 2014, 7 pgs.
The International Bureau of WIPO, International Preliminary Report on Patentability for International Application No. PCT/US2013/037213, entitled, "Natural Orifice Surgery System" dated Oct. 21, 2014, 8 pgs.
European Patent Office, The International Search Report and Written Opinion for International Application No. PCT/US2014/056563, entitled "Natural Orifice Access Device," dated Dec. 22, 2014, 13 pgs.
The International Bureau of WIPO, International Preliminary Report on Patentability, for International Application No. PCT/US2014/027258, dated Sep. 24, 2015, 6 pgs.
European Patent Office, European Search Report for European Patent No. 15182203.8, dated Dec. 15, 2015, 4 pgs.
The International Searching Authority, The International Search Report and Written Opinion of the International Searching Authority for International Application No. PCT/US2015/040798 dated Dec. 14, 2015, 21 pgs.
The International Bureau of WIPO, International Preliminary Report on Patentability and Written Opinion for International Application No. PCT/US2014/056563, entitled "Natural Orifice Access Device" dated Mar. 31, 2016, 8 pgs.
The International Bureau of WIPO, International Preliminary Report on Patentability for International Application No. PCT/US2015/040798, entitled, "Gels Having Permanent Tack Free Coatings and Methods of Manufacture" dated Feb. 2, 2017, 14 pgs.
European Patent Office, Extended European Search Report for European Patent No. 17188582.5, entitled, "Single Port Access System," dated Jan. 5, 2018, 8 pgs.
European Patent Office, Extended European Search Report for European Application No. EP 19151981.8, entitled "Natural Orifice Surgery System", dated Feb. 27, 2019, 10 pgs.

\* cited by examiner

SURGICAL ROBOTIC ACCESS SYSTEM FOR IRREGULARLY SHAPED ROBOTIC ACTUATORS AND ASSOCIATED ROBOTIC SURGICAL INSTRUMENTS

CROSS-REFERENCE TO RELATED APPLICATIONS

This application is a continuation of U.S. patent application Ser. No. 15/697,288 filed Sep. 6, 2017, which claims priority to and benefit of U.S. Provisional Application No. 62/393,305, filed on Sep. 12, 2016, the entire disclosure of which is hereby incorporated by reference as if set forth in full herein.

BACKGROUND

This application is generally directed to surgical access devices and more particularly to surgical access systems for surgical robotics or irregularly shaped instruments.

Surgical robotics has been gaining acceptance and seeks to replace or assist in particular surgical procedures. In particular, some surgical assistance provided by surgical robotics is designed to alleviate complicated or repetitive tasks. However, surgical robotics provides challenges where procedures performed by a surgeon without robotic assistance would not encounter. One such area is with surgical access devices used in surgery to facilitate the introduction of various surgical instruments into natural biological vessels, conduits, orifices, cavities, and other interior regions of the body. Surgical robotic instruments or actuators impose other restrictions that are not encountered or not a limitation with other surgical instruments or actuators, e.g., a surgeon's hand. Such challenges are further exasperated by the limited or restricted surgical area or environment. For example, the surgical environment may require an introduction of laparoscopic or particular sized instruments or actuators into the abdomen of the body and/or introduced into regions that include fluid or gas under pressure.

SUMMARY

In various exemplary embodiments, a surgical robotic access system comprises a surgical robotic access platform. The surgical robotic access platform comprises a sealing cap that sealingly conforms or engages with the irregularly shaped robotic manipulators and/or a robotic sheath while maintaining pneumoperitoneum during insertion, operation and removal of the robotic manipulator. In various exemplary embodiments, the robotic sheath is removably insertable into the sealing cap. In various exemplary embodiments, the sheath is removable, e.g., separable or can be torn, to expose the robotic manipulator or at least a portion of the robotic manipulator and/or to remove the sheath from the surgical site, the robotic access platform, the robotic manipulator or any combination thereof.

In various exemplary embodiments, a surgical robotic access system providing instrument access into a patient's body is provided. The surgical robotic access system comprises a surgical robotic access platform and a robotic sheath. The surgical robotic access platform has a proximal portion disposed externally relative to a patient's body and a distal portion positioned within a patient's body in which the proximal portion of the surgical robotic access platform includes a flexible seal. The robotic sheath has a proximal end and a distal end insertable through the flexible seal of the surgical robotic access platform. The robotic sheath also has an expandable cover disposed at the distal end of the robotic sheath and defines a cavity having proximal opening and a distal opening and through which a surgical robotic manipulator is insertable therethrough. In various exemplary embodiments, the expandable cover of the robotic sheath is arranged to encase and surround a distal end of the surgical robotic manipulator within the cavity of the robotic sheath and the flexible seal is arranged to encase and surround the expandable cover of the robotic sheath to compress the expandable cover of the robotic sheath against the distal end of the surgical robotic manipulator and thereby maintain an insufflation gas seal between the surgical robotic manipulator, the robotic sheath and the flexible seal.

In various exemplary embodiments, the sealing cap comprises a mesh or mesh lined pattern molded into a flexible seal that prevents or reduces undesired movement of the area of the flexible seal that is sealing around the robotic manipulator and/or the robotic sheath. In various exemplary embodiments, the flexible seal includes or is incorporated with a netting, mesh, webbing or interwoven strings or plastic lines to support or reinforce the flexible seal.

In various exemplary embodiments, the sealing cap includes a flexible seal fortified to resist puncture or damage from irregularly shaped or sharp robotic manipulators. In various exemplary embodiments, a protector or shield is embedded or attached to the flexible seal to protect the flexible seal, the robotic sheath, the robotic manipulator or any combination thereof. In various exemplary embodiments, the flexible seal includes shields or protectors such as sheets of resilient or puncture resistant film, fabric, plastic or the like within or on a surface of the flexible seal or arrayed at or near an access point or predefined opening through the seal. In various exemplary embodiments, the sealing cap provides laparoscopic or robotic manipulator or sheath, insufflation, and/or smoke evacuation access.

These and other features of the invention will become more apparent with a discussion of exemplary embodiments in reference to the associated drawings.

BRIEF DESCRIPTION OF DRAWINGS

The present inventions may be understood by reference to the following description, taken in connection with the accompanying drawings in which the reference numerals designate like parts throughout the figures thereof.

DETAILED DESCRIPTION

In accordance with various exemplary embodiments, a surgical robotic access system provides access for surgical robotic manipulators that includes but is not limited to robotic surgical instruments, actuators, irregularly shaped surgical instruments, and/or operative portions of a surgical robotic system or accessories thereof inserted and operating within a patient's body. The robotic manipulators are robotically controlled by the surgical robotic system autonomously or through assistance of a surgeon without a surgeon in direct contact or physically grasping the surgical robotic manipulator. The surgical robotics access system in accordance with various exemplary embodiments maintains pneumoperitoneum, patient safety and/or system integrity during installation, articulation, actuation and/or removal of the robotic manipulators.

In various exemplary embodiments, the surgical robotic access system comprises a robotic sheath that enables ease of device placement without modifications to the robotic manipulator or a surgical robotic access platform. The sheath converts the robotic manipulator and in particular, the irregularly shaped robotic manipulators into a smooth and/or uniformed shape, size, surface area or any combination thereof for insertion, manipulation and withdrawal of the robotic manipulator into a patient's body. Once the robotic manipulator is placed, in various exemplary embodiments, the sheaths may be removed to expose the robotic manipulator or at least a portion of the robotic manipulator.

Figure 1:
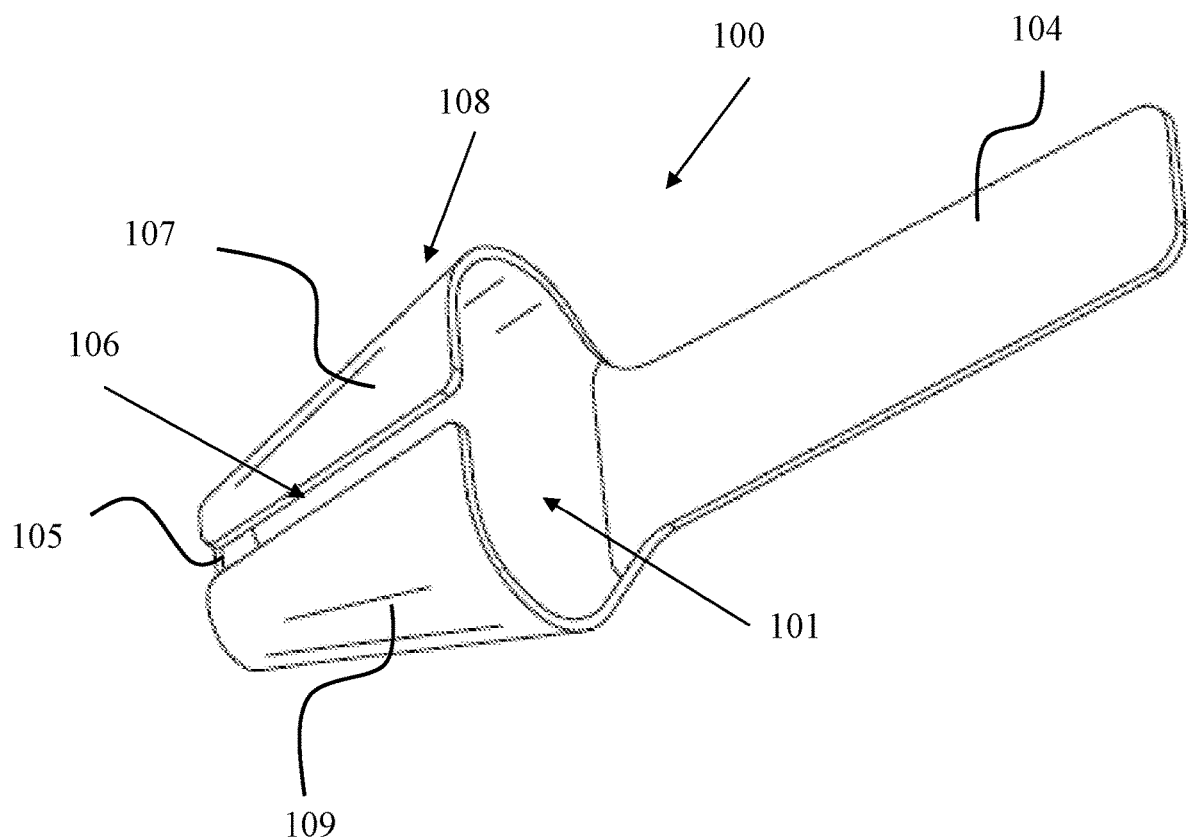
FIG. 1 is a perspective view of a robotic sheath of a surgical robotics access system in accordance with various exemplary embodiments.

Referring now to FIG. 1, a robotic sheath 100 has a proximal portion and a distal portion. The distal portion of the sheath is configured to be inserted directly through a wall or opening in a patient's body or surgical access platform. In accordance with various exemplary embodiments and described in greater detail below, e.g., in reference to FIG. 29, the surgical access platform includes a sealing cap 800 removably coupled to a retractor or protector 820. The sealing cap 800 comprises a flexible seal 804 that in various exemplary embodiments is made of a flexible material such as a gel material.

The robotic sheath includes retrieval tail 104 extending proximally from an expandable cover or compartment 108 having a distal end and a proximal end. The expandable cover defines a pocket or cavity 101 and in various exemplary embodiments, a funnel shaped cavity. The distal end of the cover includes an opening or aperture and the proximal end of the cover includes an opening. In various exemplary embodiments, the proximal opening is larger in diameter than the distal opening of the cover. The sheath includes an outer or exterior surface that is uniform and smooth. The sheath also includes an inner or interior surface that is uniform and smooth.

The cover 108 is arranged to receive a robotic manipulator, e.g., a robotic surgical instrument or actuator, irregularly shaped surgical instrument or at least a distal portion thereof inserted into the delimited or defined lumen or cavity 101. In various exemplary embodiments, the cavity is also sized and shaped to retain and support the surgical robotic manipulator. The cover includes arcuate or curved sides 107, 109 separated by a slit 106. The slit or slot 106 extends from the distal opening to the proximal opening of the cover. The slit or separation between the curved sides allows the cover or slit to enlarge or the curved sides to spread apart to thereby accommodate a wide range of robotic manipulators or surgical instruments having varying sizes, shapes, outlines, footprints and/or surfaces. In various exemplary embodiments, more than one slit is provided and with various lengths to further accommodate the contours or dimensions of the inserted manipulators. The curved sides and smooth surfaces assist in the insertion of the sheath into the body cavity or the access platform by providing a smooth interface with minimal friction between the body wall or access platform and the sheath. As such, irregular or aggressively formed manipulators are not in direct contact with the body or access platform and thus cannot damage or their potential damage to the platform or incision site is reduced. Furthermore, the smooth inner surfaces of the cover do not damage or reduces potential damage to the cover and the inserted manipulator. As such, the sheath covers or converts the irregularly shaped robotic manipulator disposed therein into a uniform and smooth shape or continuous surface to ease entry and placement of the manipulator into the body cavity.

In various exemplary embodiments, a flap 105 covers or encloses the distal opening in the cover 108. The flap is biased or removably attached to the distal end or tip of the cover 108. As such, the flap resists pressure or forces applied to the flap from an inserted manipulator. Once the flaps' bias is overcome or the flap is detached from the expandable cover, the inserted manipulator can then extend through the distal opening in the cover, unobstructed by the flap. In various exemplary embodiments, the flap once detached or biased open cannot be reclosed or reattached to obstruct the distal opening in the cover. The flap however remains attached to the distal end of the cover. As such, the sheath can be removed as a single monolithic structure. In various exemplary embodiments, the flap is flat or planar with a shape that mirrors the distal opening of the cover and provides a common and stable level or platform for the distal most end of the distal portion of the robotic manipulator. In various exemplary embodiments, the flap is attached to the cover through a living hinge.

The cover and flap separates the robotic manipulator from the body and the platform thereby protecting the manipulator and the patient. As such, the inner surface of the flap is adjacent to the distal end or tip of the robotic manipulator and the outer surface of the flap is adjacent to or exposed to the surgical site. Similarly, the inner surface of the cover is adjacent to the sides of the robotic manipulator and the outer surface of the cover is adjacent to the sides of the body wall or the access platform. The flap also provides a known target for the inserted instrument including the bias or amount of force needed to open or dislodge the flap. Using this known target data, a corresponding haptic feedback can be determined and provided by a robotic surgical system to recognize or emulate the robotic manipulator entering the body wall, platform or the engagement of the flap by the inserted robotic manipulator.

The sheath tail 104 extends from the cover and provides access or a grip area or platform to hold or stabilize the sheath for insertion or removal. The tail 104 as such stabilizes or supports the proximally extending longitudinal or elongate portion of the robotic manipulator. The tail 104 also provides a separate and sizable area or region to grasp or hold to remove the sheath from the surgical site. In various exemplary embodiments, the tail 104 is tied, coupled or otherwise attached to the robotic manipulator or a robotic sleeve surrounding the robotic manipulator to remain attached to the robotic manipulator even after the manipulator is extended or inserted through the flap 105. In various exemplary embodiments, the tail 104 is grasped, moved longitudinally until the cover and/or flap clears the outer surface of the patient's body or the access platform and then is removed from the robotic manipulator and the surgical site. As such, the robotic manipulator can then come in direct contact with the patient or access platform in which the patient or access platform seals or provides an instrument seal directly against the outer surface of the inserted robotic manipulator. In various exemplary embodiments, the tail 104 is grasped or otherwise fixed in place to hold or stabilize the sheath relative to the movement or motion of the inserted robotic manipulator and as such, as the robotic manipulator is extended distally, the sheath remains stationary being held in place by a grasper, clamp or other robotic or surgical instrumentation attached to or otherwise grasping the sheath.

Figure 2:
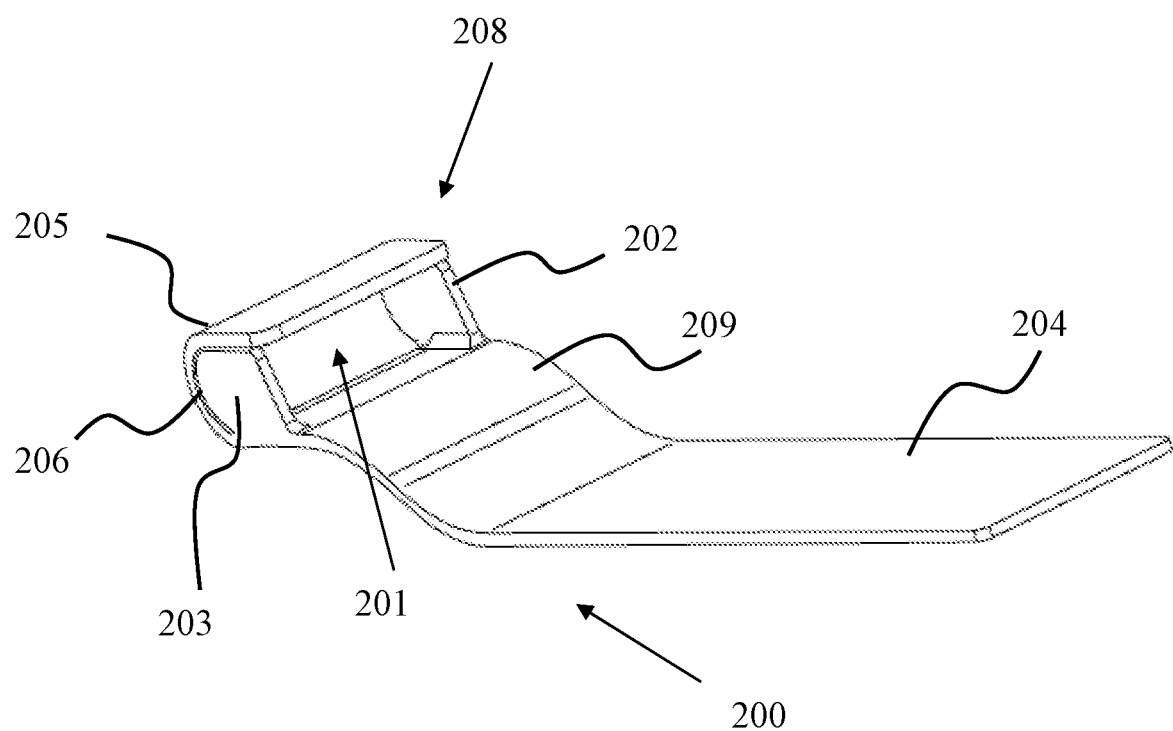
FIG. 2 is a perspective view of a robotic sheath of a surgical robotics access system in accordance with various exemplary embodiments.
Figure 3:
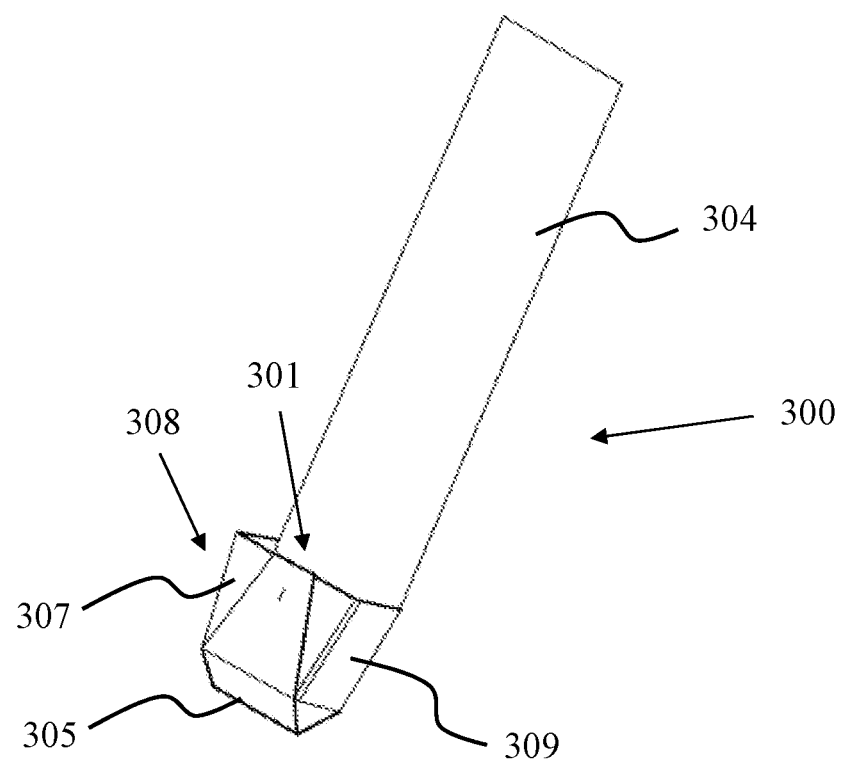
FIG. 3 is a perspective view of a robotic sheath of a surgical robotics access system in accordance with various exemplary embodiments.
Figure 4:
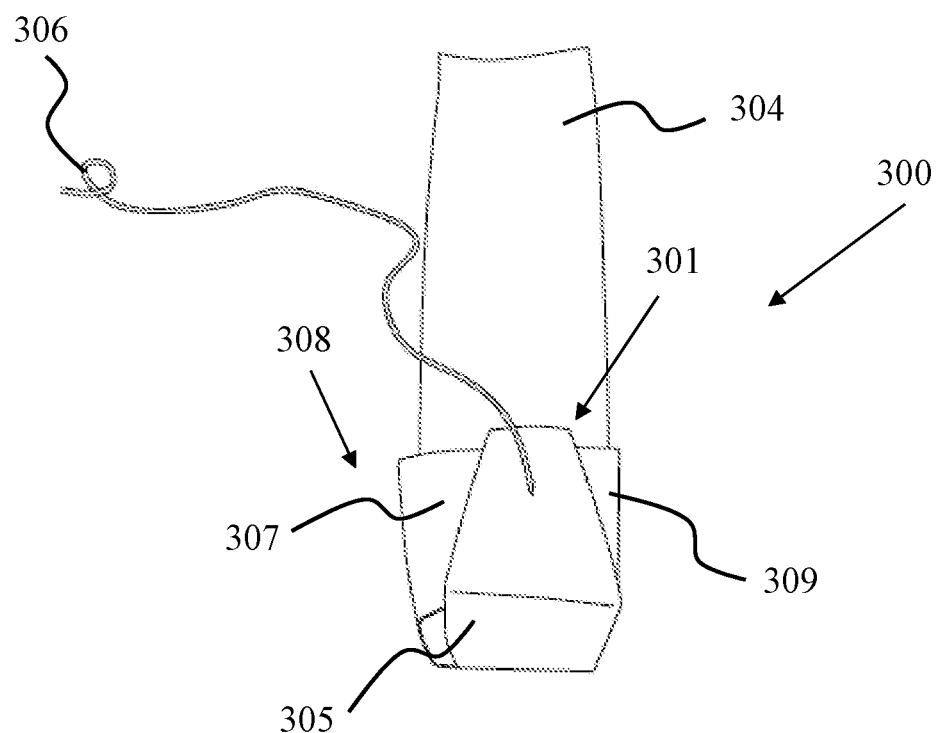
FIG. 4 is a perspective view of a robotic sheath of a surgical robotics access system in accordance with various exemplary embodiments.
Figure 5:
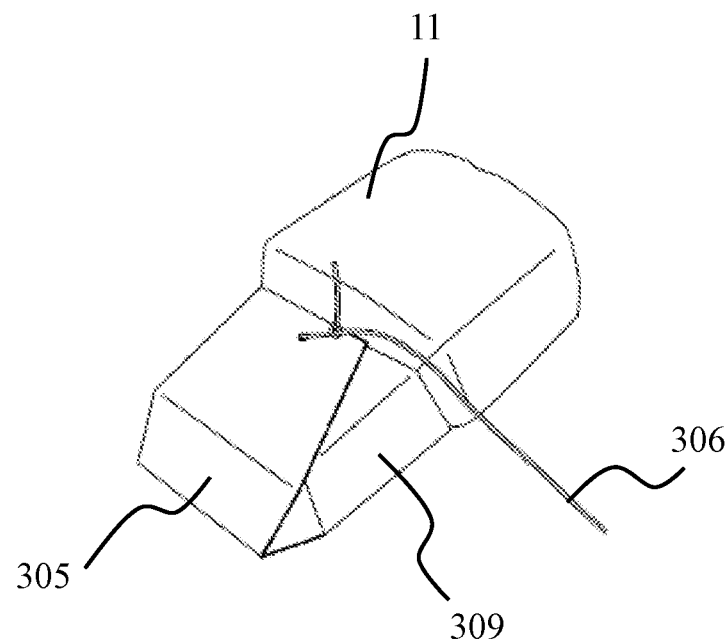
FIG. 5 is a perspective view of a robotic sheath of a surgical robotics access system in accordance with various exemplary embodiments.
Figure 6:
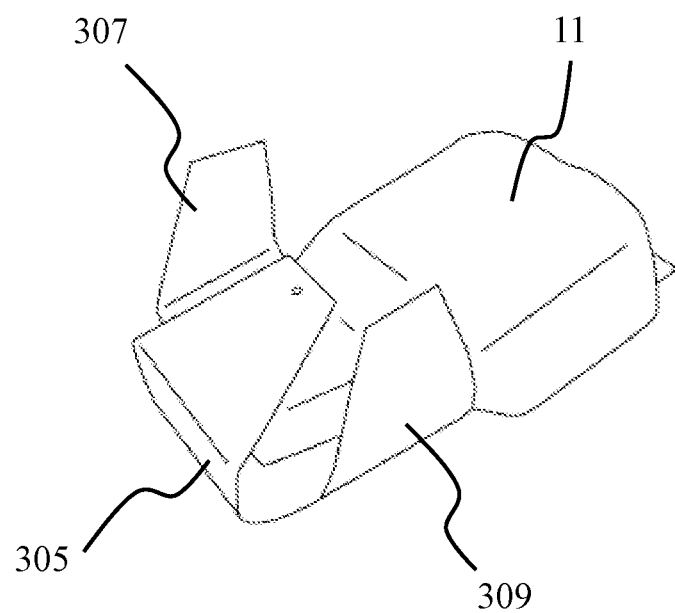
FIG. 6 is a perspective view of a robotic sheath of a surgical robotics access system in accordance with various exemplary embodiments.
Figure 7:
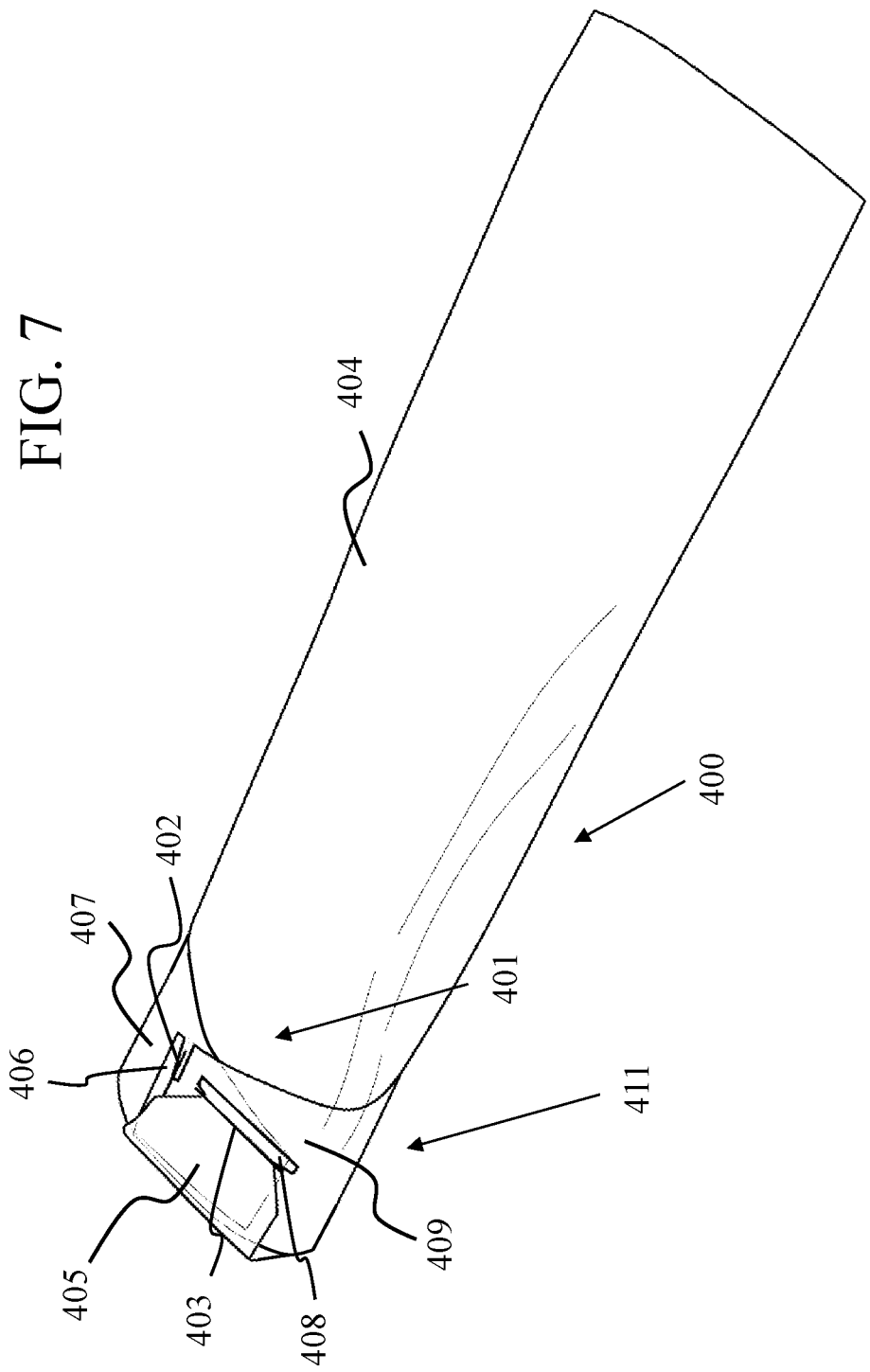
FIG. 7 is a perspective view of a robotic sheath of a surgical robotics access system in accordance with various exemplary embodiments.
Figure 8:
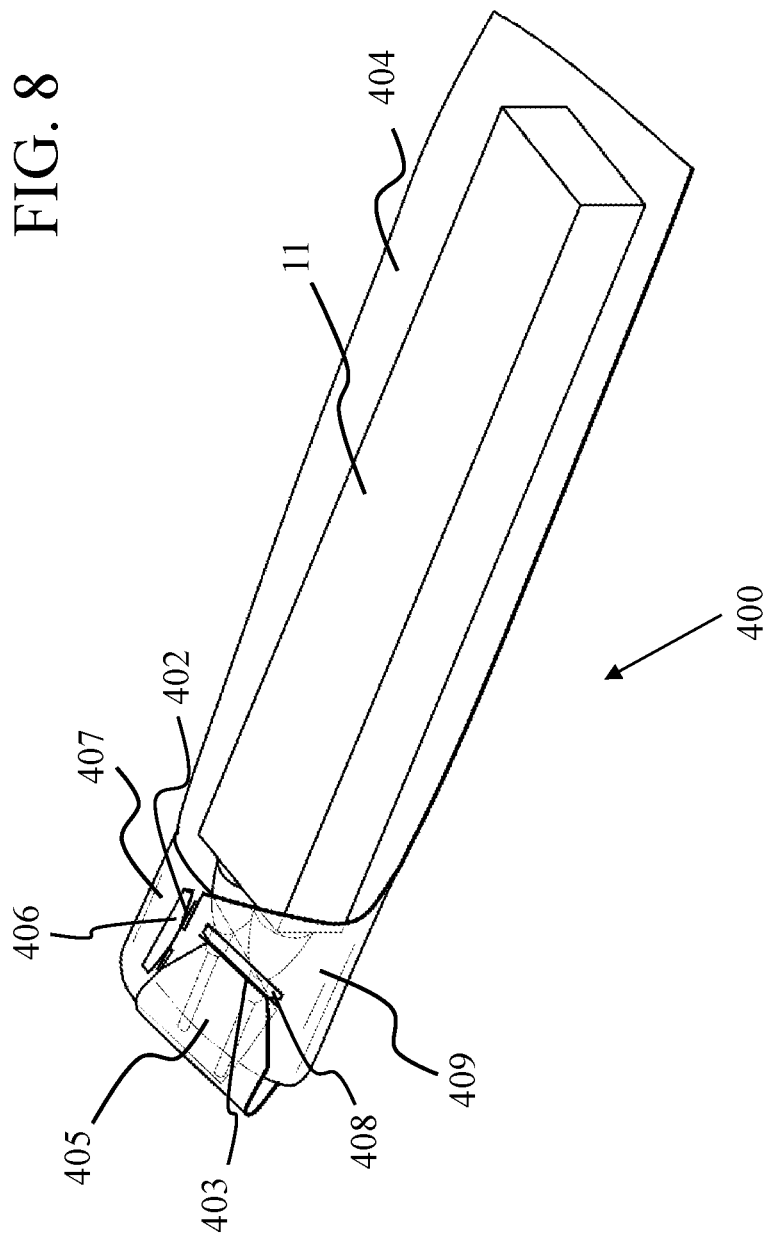
FIG. 8 is a perspective view of a robotic sheath of a surgical robotics access system in accordance with various exemplary embodiments.

Referring to FIG. 2, in accordance with various exemplary embodiments, a robotic sheath 200 includes an expandable cover or enclosure 208. The cover 208 includes a proximal opening and defines a cavity or pocket 201. In the illustrated exemplary embodiment, the cover 208 includes side flap or wall 202, an opposing side flap or wall 203 and a distal wall or flap 205 that collectively define or delimit the cavity 201. A curved slit 206 separates the side wall 202 from the distal or front wall 205 and a similar slit separates the side wall 203 from the distal wall 205 and thereby allows the cavity defined by the cover to expand and accommodate various sized and shaped manipulators inserted therein. Also, in various exemplary embodiments, the distal wall can unfold or curl away distally thereby allowing the distal end of the manipulator to extend through the now unobstructed distal opening in the cover 208.

In various exemplary embodiments, the cover is biased proximally to initially resist forces or pressures from a manipulator being moved distally but once overcome allows the distal end of the manipulator to extend there through. In various exemplary embodiments the distal wall 205 is removably attached to one or more side walls, e.g., the slits are or include perforations or the walls include a portion, bridge or connections to each other, to bias or resist the distal movement of the manipulator and the separation of the walls from each other. As such, once the bias of the distal wall is overcome or the distal wall is detached from the side walls, the distal wall can be moved or unfolded to provide unobstructed access through the distal opening in the sheath by an inserted instrument. In various exemplary embodiments, once the distal wall is unfolded or detached from the side walls, the distal wall may not be reattached or folded back to cover or obstruct the distal opening of the sheath.

Additionally, with the sheath being inserted into the access platform or through the body wall, the distal wall is biased proximally by the access platform or body wall contacting the distal wall thereby also counteracting any forces by the manipulator being inserted, enclosing the cavity and protecting the distal end of the inserted robotic manipulator.

A tail 204 extends proximally from the cover 208 to support the robotic manipulator and provides a removal or insertion support for the deployment of the sheath 200. The tail also includes a curved connector portion 209 connected to the cover 208. The curved connector provides additional lateral or radial space between the robotic manipulator and the sheath and thus allows easier access and attachment of the robotic manipulator to the sheath. The curved connector also spaces the tail from the robotic manipulator to further facilitate accessibility of the removal or insertion area of the tail used to assist in the deployment and/or withdrawal of the sheath and the robotic manipulator.

Referring now to FIGS. 3-6, the sheath 300 includes an expandable cover 308 defining a cavity or pouch 301 therein. The cavity is arranged to accommodate a robotic manipulator inserted or seated therein. The cover 308 is a tri-fold arrangement having first and second side folds or walls 307, 309 and a center or middle fold or wall 305. The side folds protect or cover the sides of the robotic manipulator inserted therein. The middle fold covers a distal opening of the cover 308. In various exemplary embodiments the first, second and middle folds are removably connected to each other and in various exemplary embodiments, the removable connection includes a release line or cord 306. In various exemplary embodiments, proximal movement of the release line disengages or separates the removable connection between the folds. As such, the middle fold 305 is released and can be moved distally to uncover or not obstruct the distal opening of the cover 308. In various exemplary embodiments, all the folds of the cover are disengaged and thereby separating all the folds from each other and unfolding or opening the cover or cavity.

In various exemplary embodiments, the release cord or line disengages the middle fold from the first and second folds separating the first and second folds from the middle fold. The release line remains connected to the middle fold thereby allowing the regulation of the movement of the middle fold relative to the first and second folds. As such, movement of the middle fold may be restricted as the sheath is inserted and at a particular depth or timing, the middle fold is allowed move completely away from the first and second folds to expose the distal end and allow unobstructed deployment of the inserted manipulator through the sheath. Movement of the middle fold may also be restricted to enlarge the cavity defined by the folds to accommodate larger or various sized and shaped instruments beyond the initial dimension or shape of the initial cavity defined by the folds. However, the middle fold being restricted and in place continues to protect the distal end of the inserted manipulator and facilitates entry of the sheath through the access device.

In various exemplary embodiments, the release line disengages one or more of the folds from one or more of the rest of the folds to provide different access or exposure of the robotic manipulator to the surgical site or to expand portions of the cavity as desired to accommodate a particular robotic manipulator. In various exemplary embodiments, one or more release lines are attached to one or more folds and in various exemplary embodiments a release line is connected to each fold thereby allowing individual and selective operation of the folds relative to each other and dynamically adjust the cavity and exposure of robotic manipulator as required. In various exemplary embodiments, the connection of the folds and the release line is a perforation such that movement of the release line separates portions of the middle fold along the perforation to releasably disengage the release line from the middle fold. In various exemplary embodiments the connection, disengagement of the connection or both are selectively and operationally activated to incrementally, partially or fully expand the cavity of the sheath and/or separate or unfold the sides or walls of the sheath and/or the flap. In various exemplary embodiments, once separated from a wall or fold, the walls or folds cannot be reattached and thus the sheath 300 can be removed from the surgical site to further prevent any inadvertent obstruction, leak path or restriction at the surgical site. A tail 304 extends proximally from the cover 308 to support the robotic manipulator and provides a removal or insertion support for the deployment of the sheath 300.

Referring to FIGS. 7-11, in accordance with various exemplary embodiments, a robotic sheath 400 includes an expandable cover 411 having curved side walls 407, 409 removably connected to each other through interfacing cutouts and tabs. A center wall 405 is removably connected to one or both of the side walls 407, 409. In various exemplary embodiments, the center wall includes foldable or deformable tabs 408 insertable into cutouts or apertures 403 in one or more of the side walls to removably connect the center wall to one or more of the side walls. The cover defines or delimits a cavity or enclosure 401 in which a robotic manipulator or at least a distal portion thereof is arranged to be seated therein. In various exemplary embodiments, one or more of the side walls includes foldable or deformable tabs insertable into cutouts or apertures in one or more of the side walls to removably connect one of the side walls to the other one of the side walls. In the illustrated exemplary embodiment, the side wall 407 includes an aperture or cutout 402 and the side wall 409 includes a deformable tab 406 insertable into the aperture 402 to removably connect the side walls 407, 409 together.

The connection between the center and side walls, e.g., the spacing between walls or the spacing between the tabs and apertures of the walls, the resilient or flexible material of the walls, or a combination thereof allows the cavity defined by the cover to expand to accommodate various sized and shaped robotic manipulators inserted therein. Also in various exemplary embodiments, the center wall can unfold or curl away distally thereby allowing the distal end of the instrument to extend through the now unobstructed distal opening in the cover. The cover is biased proximally to resist forces or pressures from a robotic manipulator being moved distally.

Figure 9:
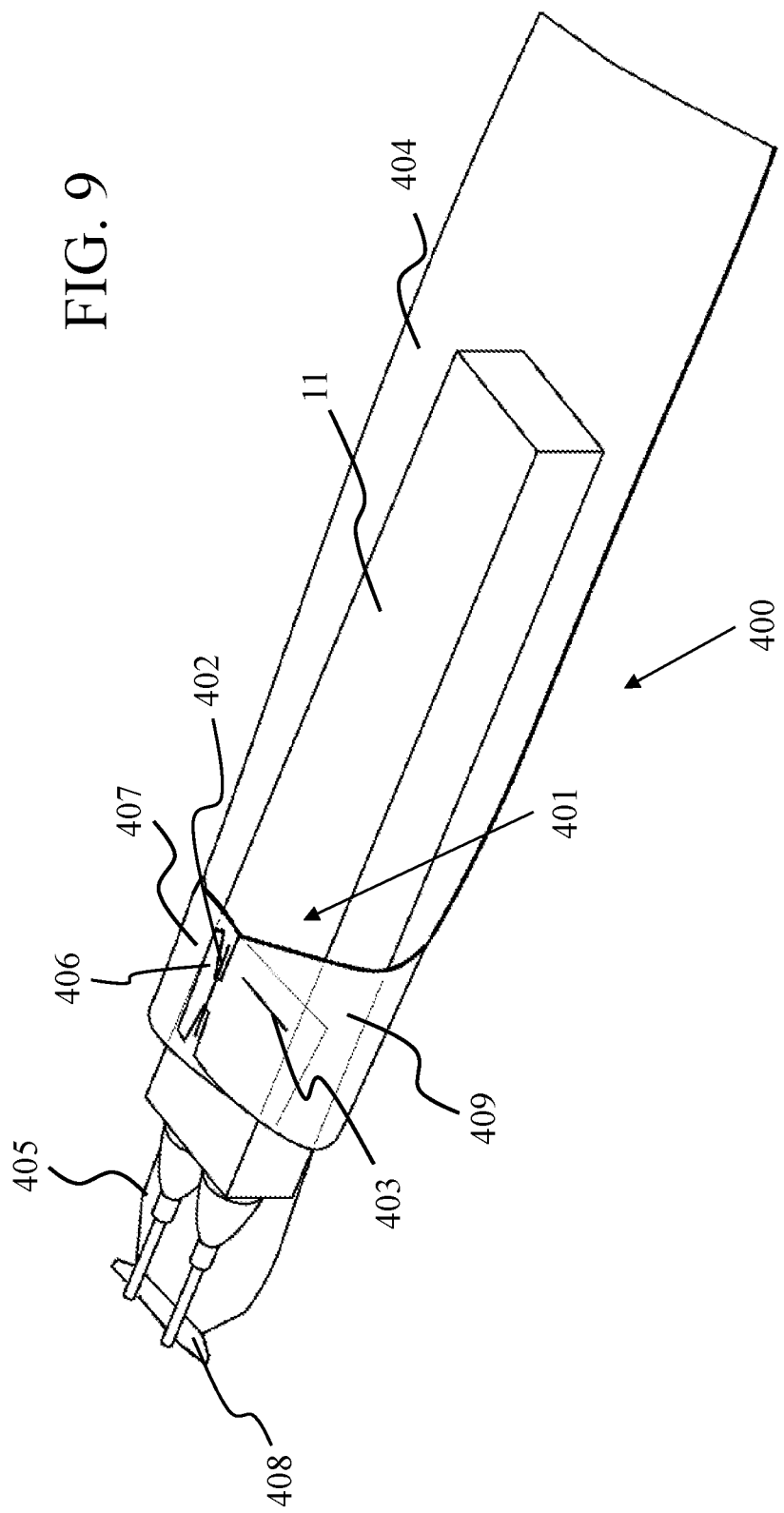
FIG. 9 is a perspective view of a robotic sheath of a surgical robotics access system in accordance with various exemplary embodiments.
Figure 10:
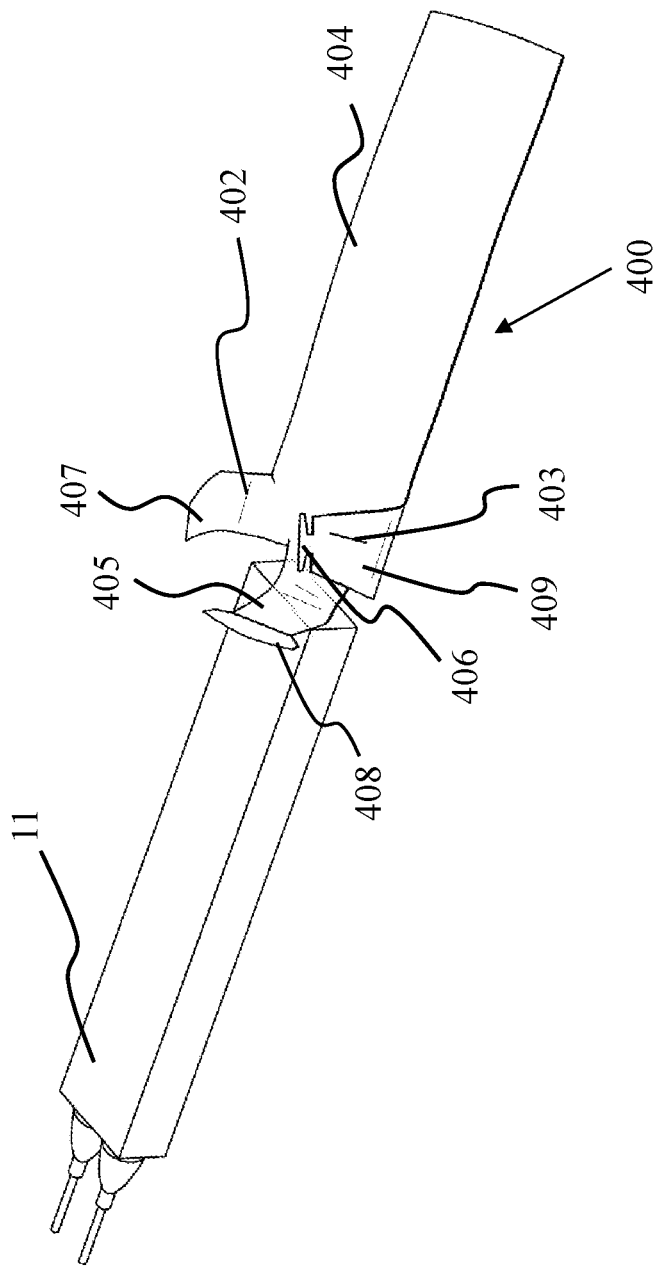
FIG. 10 is a perspective view of a robotic sheath of a surgical robotics access system in accordance with various exemplary embodiments.
Figure 11:
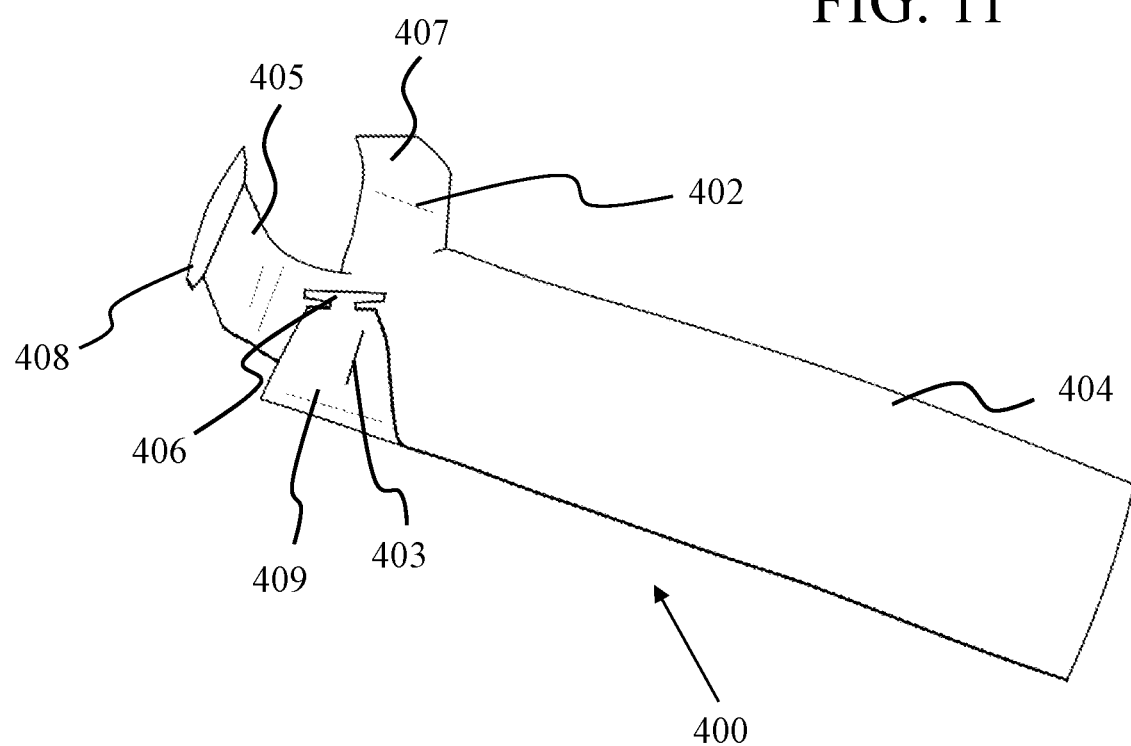
FIG. 11 is a perspective view of a robotic sheath of a surgical robotics access system in accordance with various exemplary embodiments.

Once the bias of the center wall is overcome or the center wall is detached from one of the side walls, the center wall can be moved or unfolded to provide unobstructed access through the distal opening in the sheath by an inserted robotic manipulator. In various exemplary embodiments once the center wall is unfolded or detached from one of the side walls, the center wall may not be reattached or folded back to cover or obstruct the distal opening of the sheath. In various exemplary embodiments, the deformable or frangible tabs or apertures are disengaged or torn from each other to unfold or detach the sheath from the robotic manipulator. As shown in FIG. 9, only the center wall may be operationally detached from one or both of the side walls to provide unobstructed access through the opening in the sheath. With the side walls attached to each other, however, the sheath can remain connected to the robotic manipulator to further protect the manipulator or patient during operation and withdrawal of the manipulator. As illustrated in FIGS. 10-11, all the folds or wall may be detached from each other to, for example, ease removal of the sheath from the robotic manipulator and/or the surgical site, to provide different access or exposure of the robotic manipulator to the surgical site or to expand portions of the cavity as desired to accommodate a particular robotic manipulator. The center wall in various exemplary embodiments may also be reattached to the side wall by inserting the tab 408 into aperture 403 of side wall 409 to further assist in the removal of the manipulator from the surgical site. Similarly, the side walls may be reattached by inserting tab 406 of side wall 409 into aperture 402 of side wall 407. A tail 404 extends proximally from the cover 411 to support the robotic manipulator and provides a removal or insertion support for the deployment of the sheath 400.

Figure 12:
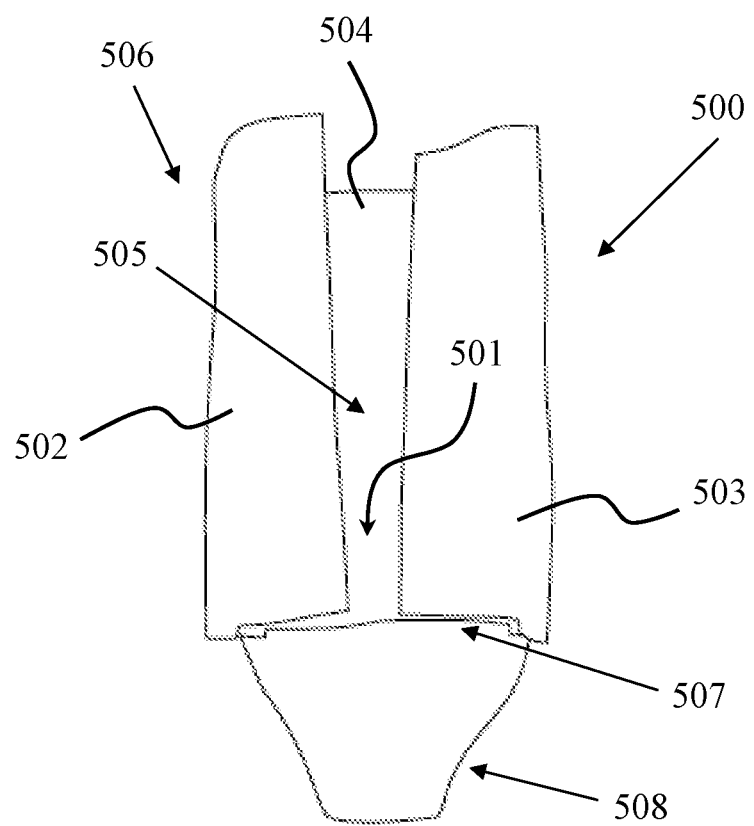
FIG. 12 is a side view of a robotic sheath of a surgical robotics access system in accordance with various exemplary embodiments.

Referring to FIG. 12, the sheath 500 includes a proximal cover 506 and a distal cover 508. The proximal cover includes an elongate portion or tail 504 with arcuate sidewalls 502, 503 that cover portions of a robotic manipulator inserted therethrough. A vertical slit 505 extends between the sidewalls and thus allows the side walls to move away from each other. Thus, the proximal cover can expand to accommodate various sized and shaped robotic manipulators. The proximal cover along with the distal cover extends the support and conversion of the robotic manipulator and extends the protection of the robotic manipulator, the patient and an access platform. As such, the curved sidewalls 502, 503 with smooth outer surfaces further assist in the insertion of the sheath into the body cavity or the access platform by providing a smooth continuous interface with minimal friction between the body wall or access platform and the sheath. Furthermore, the smooth inner surfaces of the cover do not damage or reduces potential damage to the cover and the inserted manipulator.

A horizontal slit 507 separates the sidewalls 502,503 of the proximal cover from the distal cover and thereby further allows the proximal cover to expand and the distal cover to separate from the proximal cover. The distal cover includes a proximal opening connecting to a central lumen or cavity 501 delimited by the proximal cover 506. The distal cover 508 also includes a distal opening coupled to the proximal opening of the distal cover and also defines or delimits a cavity or lumen through the distal cover 508. In various exemplary embodiments, the cavity of the distal cover 508 and the cavity of the proximal cover 506 are interconnected and in which the robotic manipulator is inserted, seated within and moved there through. In various exemplary embodiments, the distal cover 508 is arranged to swing, pivot or be displaced away from the proximal cover 506 and thereby provides an unobstructed pathway from a proximal opening in the proximal cover to the distal opening in the proximal cover. The tail 504 surrounded by side walls 502, 503 extends from the distal cover 508 to support the robotic manipulator and provides a removal or insertion support for the deployment of the sheath 500.

In various exemplary embodiments, the distal cover 508 is hemispherical to ease placement of the sheath and in various exemplary embodiments has a proximal opening but no distal opening to further define the cavity in which a robotic manipulator is held, enclosed or encased therein. As such, in various exemplary embodiments, the entire distal cover is displaceable away from the proximal cover to provide an unobstructed pathway out from the proximal cover.

Figure 13:
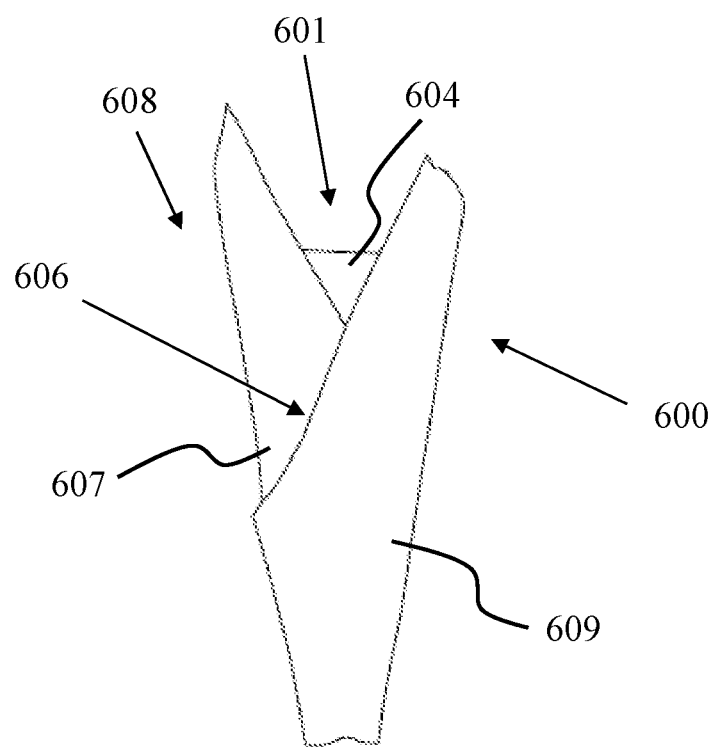
FIG. 13 is a side view of a robotic sheath of a surgical robotics access system in accordance with various exemplary embodiments.

In FIG. 13, the sheath 600 is a monolithic sheet with ends 607, 609 wrapped around each other and defining a cavity or lumen 601. The lumen connects a proximal opening to a distal opening of the sheath. The proximal opening has a diameter larger than the diameter of the distal opening. The sheath provides a proximal cover 608 having a frustoconcial shape to facilitate insertion of the sheath. In various exemplary embodiments, the distal end includes a movable distal wall covering or obstructing the distal opening of the sheath. In various exemplary embodiments, a tail 604 extends from a portion near the proximal opening of the sheath or along the entire length of the sheath to support the robotic manipulator and provides a removal or insertion support for the deployment of the sheath. The ends of the sheath at the overlap 606 are movable relative to each other and thereby allowing expansion of the sheath and thus accommodating various sized and shaped instruments inserted therein. Apertures and detents, ratchet like mechanisms or the like in various exemplary embodiments interconnect the ends 607, 609 of the sheath to provide incremental and operational adjustment or enlargement of the cavity 601 of the sheath. As such, the sheath 600 extends the support and conversion of a robotic manipulator to a uniform, smooth and/or continuous surface or shape and extends the protection of the robotic manipulator, the patient and an access platform.

Figure 14:
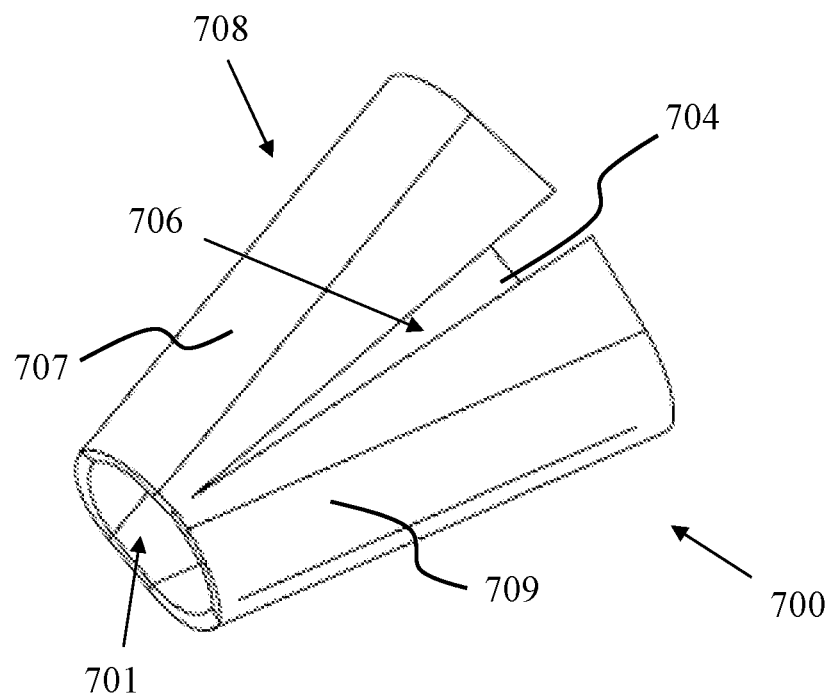
FIG. 14 is a perspective view of a robotic sheath of a surgical robotics access system in accordance with various exemplary embodiments.
Figure 15:
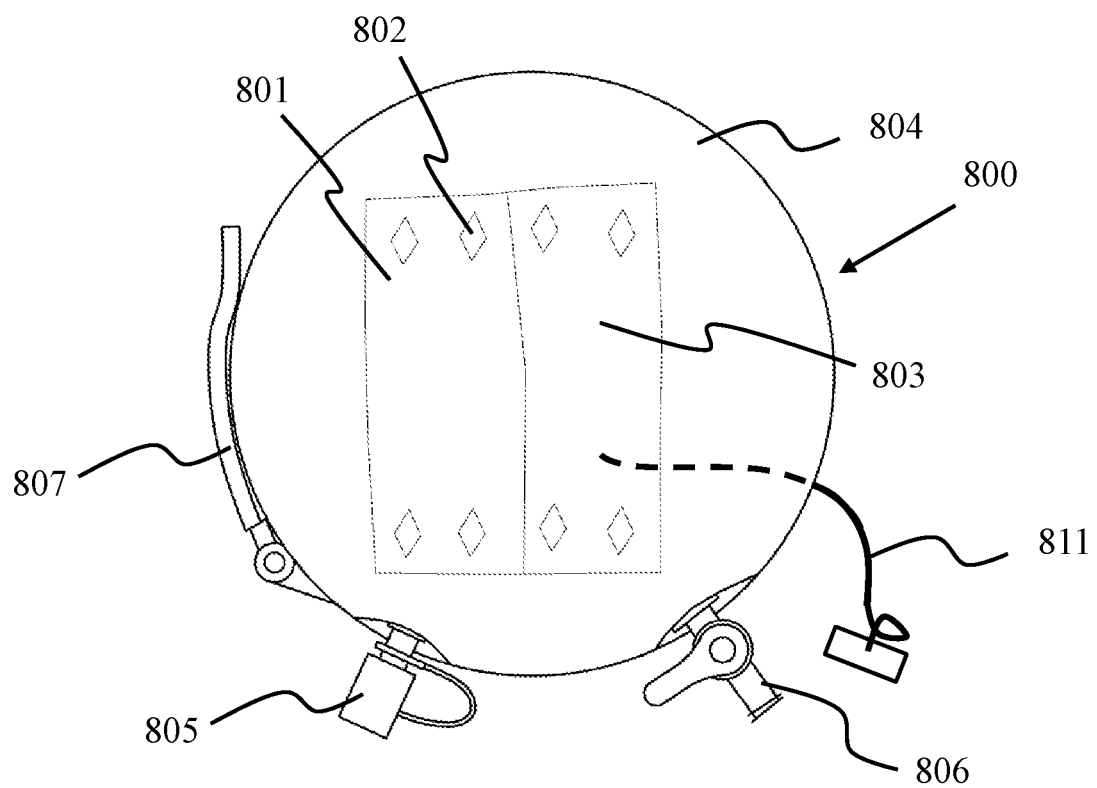
FIG. 15 is a top view of a sealing cap of a surgical robotics access system in accordance with various exemplary embodiments.
Figure 16:
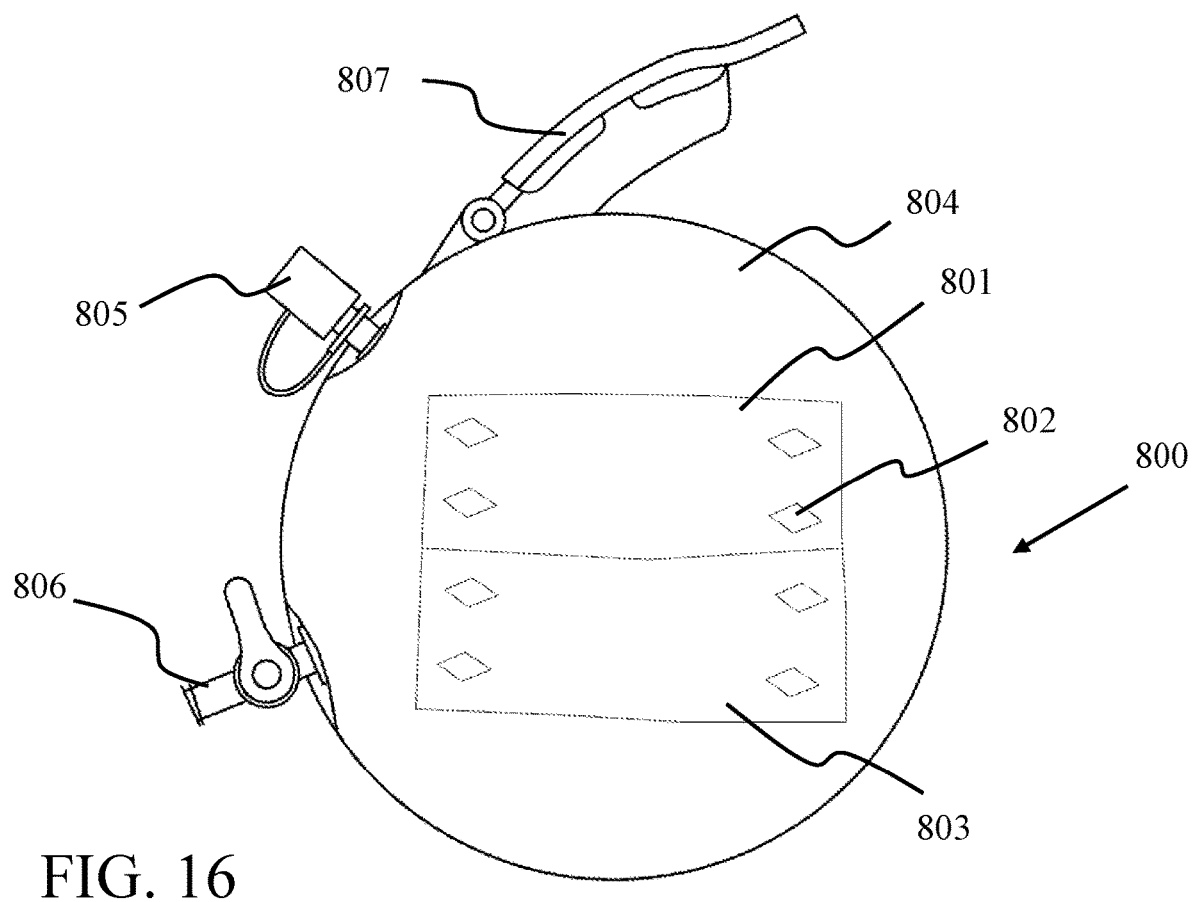
FIG. 16 is a top view of a sealing cap of a surgical robotics access system in accordance with various exemplary embodiments.
Figure 17:
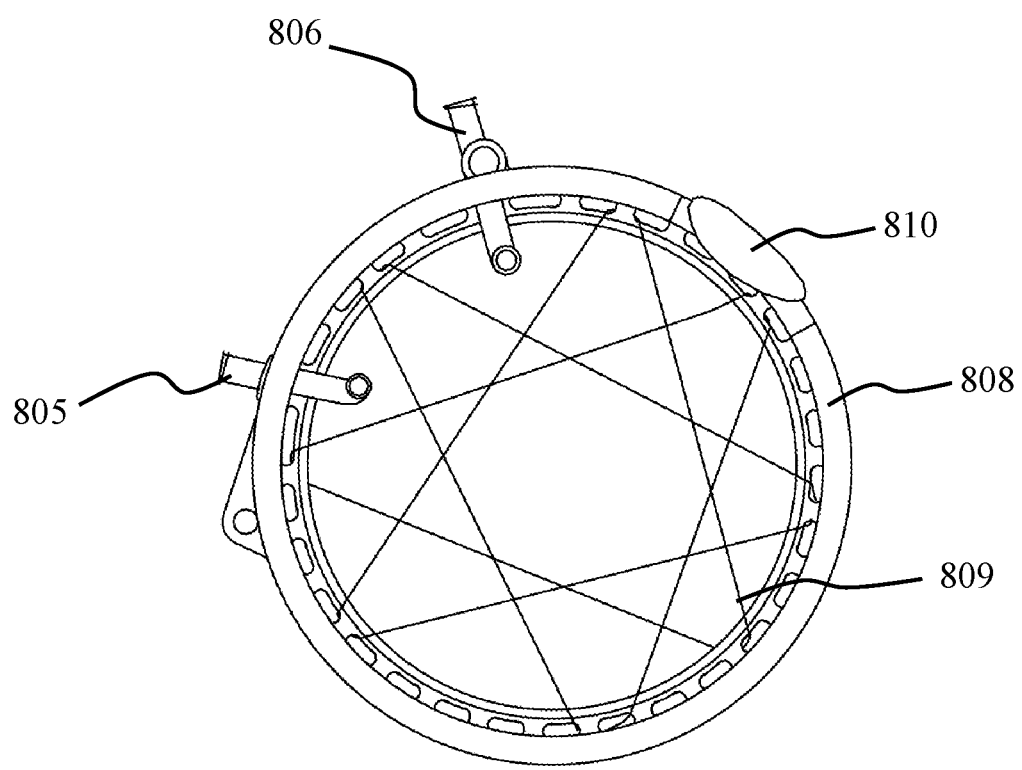
FIG. 17 is a bottom view of portions of a sealing cap of a surgical robotics access system in accordance with various exemplary embodiments.
Figure 18:
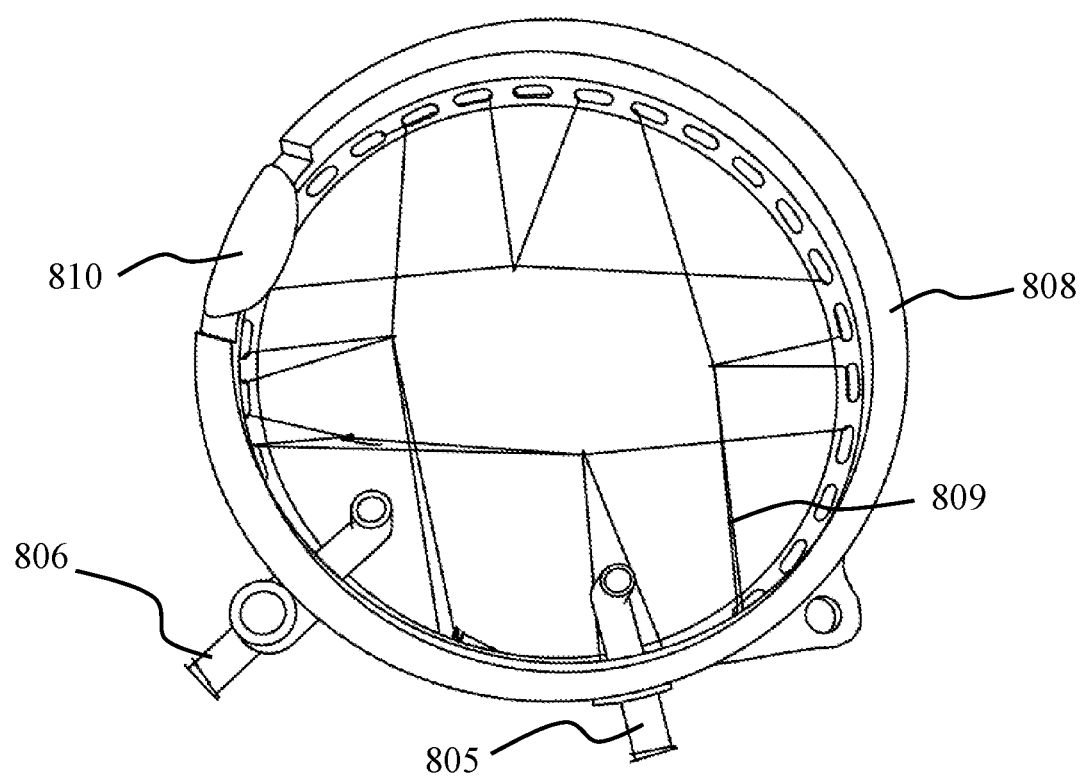
FIG. 18 is a bottom view of portions of a sealing cap of a surgical robotics access system in accordance with various exemplary embodiments.

In FIG. 14, a sheath 700 includes a proximal opening and a distal opening with a central lumen 701 connecting the openings together. Arcuate side sections or walls 707, 709 define the central lumen or cavity in which a robotic manipulator may be inserted into. The side walls 707, 709 protect the inserted robotic manipulator. One or more slits 706 extend from the proximal opening to the distal opening and thereby allows the cover 708 or its side walls to move away from each other and thus expand thereby accommodating various sized and shaped robotic manipulator. The cover 708 has a frustoconcial shape to facilitate insertion of the sheath. In various exemplary embodiments the side walls are biased closed or towards each other and thereby provide a clamping or further fortifying the securement of the sheath to the robotic manipulator. In various exemplary embodiments, the side walls are attached or incorporated with spring-like material, elastic strips or fibers or shape memory alloy to bias the side walls or the cover closed or towards each other. Likewise, the distal and proximal openings of the sheath can also expand to accommodate various sized and shaped robotic manipulators being inserted through the sheath. The side walls 707, 709 are connected to each other at a distal end and thus expand proximally to distally as needed to accommodate the inserted robotic manipulator. In various exemplary embodiments, the connection is frangible or detachable to allow complete separation of the side walls from each other. Additionally, the side walls separated from each other eases removal of the sheath from the surgical site, the surgical robotic manipulator or both. In the illustrated exemplary embodiment, the sheath does not include a flap obstructing the distal opening of the sheath. In various exemplary embodiments, portions of the side walls overlap each other and as such, the side walls overlapping each other cover portions of the slit. A tail 704 surrounded by side walls 707, 709 and/or extending from the cover 708 supports the robotic manipulator and provides a removal or insertion support for the deployment of the sheath 700. As such, the sheath 700 extends the support and conversion of a robotic manipulator to a uniform, smooth and/or continuous surface or shape and extends the protection of the robotic manipulator, the patient and an access platform.

It should be appreciated that the described features and details of the various exemplary embodiments are illustrative and can be applicable to the other various exemplary embodiments although not explicitly shown or described. Accordingly, combinations of exemplary embodiments and features or aspects of various exemplary embodiments or combinations of exemplary embodiments described can also be applicable to the other exemplary embodiments. Any missing described combination or feature is for clarity or to avoid repetition.

The following remaining description provides features or aspects applicable to the various sheath exemplary embodiments and thus the below described sheath or sheaths refers to all the sheath exemplary embodiments, e.g., sheaths 100-700. In various exemplary embodiments, the tail or the elongate portion of the sheath acting or operating as a tail may be shorten or have a length equal or less than the length of the cover as needed, e.g., where operating space is limited or greater flexibility or mobility is needed. Similarly, in various exemplary embodiments the tail of the various sheaths may be removed. In various exemplary embodiments, the tail is elongate and is longer than the cover as applicable, e.g., where larger coverage or protection of the robotic manipulator is desired and/or larger removal or insertion area for the deployment of the sheath is desired. In various exemplary embodiments, the tail extends proximally from the expandable cover and is elongate and planar and is lengthwise longer than the expandable cover. In various exemplary embodiments, the tail of the various sheaths includes a curved or raised connector portion connected to the cover. The curved connector provides additional lateral or radial space of the robotic manipulator allowing easier access and attachment of the robotic manipulator to the sheath and spaces the tail from the robotic manipulator to further facilitate accessibility of the removal or insertion area of the tail to assist in deployment of the sheath.

In various exemplary embodiments, the sheath is made of a flexible and compressible material to conform to the robotic manipulator to affect an instrument seal due to compressive forces of the body wall or the access platform on the sheath. In various exemplary embodiments, the robotic sheath is made of a flexible and compressible material with a lower durometer than the surgical robotic manipulator and is arranged to conform to the surgical robotic manipulator due to compressive forces of the flexible seal of the surgical robotic access platform arranged to compress the cavity of the expandable cover of the robotic sheath against the distal end of the surgical robotic manipulator and to maintain an insufflation gas seal between the surgical robotic manipulator. In various exemplary embodiments, the sheath includes a funnel-shaped cover to provide or ease access of the sheath through the body wall or access platform.

The various sheaths in various exemplary embodiments include a cover or an expandable portion to accommodate various sized and shaped robotic manipulators. The sheath covers irregularly shaped, sharp, rough, textured, or other manipulators having undercuts, protrusions, detents or other similar extremities that may damage the patient and/or access platform or create leak paths. As such, the sheath converts irregular shaped robotic manipulators to a more uniform or smooth shape for insertion, operation and removal without interfering or unduly limiting the range of operation of the robotic manipulator. The sheath thus protects the patient, the robotic manipulator and the access platform.

The expandable portion of the sheath in various exemplary embodiments includes side walls to protect the outer surface or region of the robotic manipulator. The expandable portion includes an opening that facilitates insertion of the robotic manipulator to be seated therein. The distal opening facilitates access of the robotic manipulator through the sheath. The side walls also provide a smooth and uniform outer surface to protect the entry point or area into the body or access platform. The outer surface also minimizes leak paths or facilitates sealing. The outer surface also facilitates entry and removal of the sheath.

The side walls in various exemplary embodiments define a cavity wherein the distal end of the robotic manipulator can be seated to secure or attach the sheath to the robotic manipulator. The cavity also provides an area or region in which a distal force applied by the robotic manipulator is applied or experienced by the sheath. In various exemplary embodiments, the cavity or lumen of the various sheaths is filled or lined with foam, inflated bladders or gel cushions to further protect the instrument seated within the cavity. The foam or other protective material is lined, affixed or adhered to portions of the cover to ensure the protective material moves away from the path of the inserted instrument or follows movement of the cover while remaining affixed to the cover to avoid obstructions or debris as the cover or portions thereof are displaced. In various exemplary embodiments, the protective material is made of a material different from the material of the expandable cover and has a lower durometer than the material of the expandable cover. The various sheaths in various exemplary embodiments include an inner surface that is smooth and uniform to facilitate entry, removal and passage of the robotic manipulator through the sheath. The inner surface also protects or does not harm the robotic manipulator inserted therein.

In various exemplary embodiments, the slit or separation between the side walls or the expandable portion of the various sheaths provides an exit region for the sheath to be removed or separated from the robotic manipulator. In various exemplary embodiments, the sheath is removed from the robotic manipulator and in which case the robotic manipulator remains stationary as the sheath is separated from the instrument. With the robotic manipulator remaining stationary, manipulation or placement of the robotic manipulator does not have to be performed or in some cases performed again. As such, operation times or steps can be reduced or avoided. Also, additional space or range of movement for the robotic manipulator is not required to perform the separation of the sheath which can be an issue in the limited confines of the surgical space or the given access platform.

In various exemplary embodiments the cover of the various sheaths are made of a spring like material and thus is arranged to return to its original shape or position and thus provides a clamping or compression force upon the inserted robotic manipulator to ensure the cover remains in place protecting the distal end of the robotic manipulator. In various exemplary embodiments, portions of the sheath, e.g., the walls, folds or flaps or the proximal cover and the distal cover, are made of different materials from each other to accommodate particular robotic manipulators and their operation. For example, one wall of the sheath is made of a rigid material to protect a particular portion of the robotic manipulator requiring enhanced protection and a different wall of the sheath is made of a soft or less rigid material to enhance conformance of the sheath to the robotic manipulator.

In various exemplary embodiments, the various sheaths are molded into a shape or outline with the outer surface being continuous, uniform and smooth to ease insertion and placement. The various sheaths include an inner surface forming a cavity or housing for the placement, protection, support and ultimately an entryway for the robotic manipulator. As such, the robotic manipulator and in particular the sharp or irregularly shaped manipulators can be inserted into a surgical site without compromising the integrity of the access system or patient safety. In various exemplary embodiments, the sheath is removed or portions thereof exposing the robotic manipulator for entry into the surgical site.

In various exemplary embodiments, the integrity, shape, dimension or outline of the cavity of the various sheaths can be maintained and thus disrupted by or at a single point or area by an attachment or release mechanism. In various exemplary embodiments, a release line is provided at a release area such that after insertion of the sheath, the release line or mechanism is activated remotely or externally from the sheath or outside the patient to cause the cavity to unfold, separate, tear or breakaway and thus facilitating removal of the sheath and/or exposing or not obstructing the robotic manipulator or portions thereof. In various exemplary embodiments, distal movement of the tail of the sheath causes the cavity or portions of the sheath to unfold, breakaway, separate or tear and thus allowing quick removal of the sheath and exposure of the robotic manipulator.

In various exemplary embodiments, the portions are held together by coupling or an interconnection or connector, such as a releasable adhesive, heat bond, mechanical interlocks, magnets or other similar non-permanent or detachable mechanisms to allow the separation of portions of the sheath as desired. The connection or interlocks may include notches, tabs, detents or other similar defects on portions or ends of the cover to create or increase the mechanical interlock of the cover ends. Ball and socket, opposing hooks, ratchets, spring pins, or other connector configurations may also be provided to lock or connect portions of the sheath together. Alternatively, in various exemplary embodiments, the portions of the sheath, e.g., cover ends or walls, may be left uncoupled or separated and not connected. In various exemplary embodiments, the coupling, connector or interconnection of the portions of the sheath provides a one-way incremental and operational adjustment of the portions of the sheath, e.g., the cover, lumen or cavity, that once adjusted or manipulated, the coupling or connector is unable to be reattached or readjusted, e.g., once enlarged is unable to be contracted.

In various exemplary embodiments, the coupling, connector or interconnection of portions of the sheath is used to temporarily maintain a specified sheath shape or size. In various exemplary embodiments, releasing, disengaging or removing the coupling, e.g., by pulling a cord or manipulating a release actuator connected to the coupling, connector or interconnection, after insertion of the sheath would unfold or deploy the sheath or portions thereof to thereby facilitate removal of the sheath, access for the robotic manipulator, enlargement of the cavity or any combination thereof. In various embodiments, the disengagement may be incremental, one-way or both. In various exemplary embodiments, moving or pulling the tail or proximal end of the sheath proximally would unfold or deploy the sheath such as tearing or disengaging the interconnection between the sides or folds of the sheath. In various exemplary embodiments, the sheath may include one or more folds, walls or flaps that may be folded, formed or interconnected into a desired shape and dimension to accommodate the robotic manipulator or surgical site. In various exemplary embodiments, the size and shape of the spacing or slits between the folds, walls or flaps may be formed or temporarily connected into a desired shape and dimension to accommodate the robotic manipulator or surgical site. In various exemplary embodiments, the sheath may include a proximal cover, a distal cover or both with different sizes and shapes and defining or delimiting similar or different sizes and shapes of cavities or lumens to accommodate a particular robotic manipulator. In various exemplary embodiments, the sheath may include a proximal cover, a distal cover or both with similar sizes and shapes and defining or delimiting similar or different sizes and shapes of cavities or lumens to accommodate a particular robotic manipulator.

Additionally, with the sheath being inserted into the access platform or through the body wall, the center wall, fold, flap and/or cover is biased proximally by the access platform or body wall contacting the fold, wall, flap and/or cover thereby also counteracting any forces by the robotic manipulator being inserted, enclosing the cavity and encasing and protecting the inserted robotic manipulator.

In various exemplary embodiments, the robotic manipulator is moved to separate the sheath from the robotic manipulator. With the robotic manipulator causing the separation, a separate actuator or similar engagement portion can be avoided. In particular, a separate actuator is not required to access the tail of the sheath to remove the sheath once the instrument is placed at the surgical site.

The different or varied robotic sheaths may be used for or to identify different robotic manipulators or other identifying indicia of the robotic manipulator operation, surgical robotic system or surgical procedure. In various exemplary embodiments, the sheath is made from molded silicone, rolled plastic shim material, folded films or any combination thereof. In various exemplary embodiments, the sheath is cost effective and can be single-use disposable for each access or placement of the sheath. In various exemplary embodiments, the slits or spacing or distance between the folds, walls or flaps are constant or continuous. In various exemplary embodiments, the distance between the folds, walls or flaps is between 2 to 4 millimeters.

Referring now also to FIGS. 15-29, in various exemplary embodiments, a surgical robotic access system comprises a surgical access platform. The surgical access platform comprises a flexible seal 804 that sealingly conforms or engages with the robotic manipulators and/or the sheath while maintaining pneumoperitoneum during insertion, operation and removal. The flexible seal in various exemplary embodiments is contained, integrated or attached to a cap ring or cover 808 to form a sealing cap 800.

The sealing cap 800 in various exemplary embodiments is incorporated with or removably attached to a retractor or protector 820 that provides retraction and/or protection of the incision or opening in the patient. In various exemplary embodiments, the retractor includes a sleeve or tube 816 extending between an inner ring 815 placed inside the patient and an outer ring 817 placed outside the patient. Both rings can be rigid, flexible or any combination thereof. The sleeve is flexible and cylindrical. In various exemplary embodiments, the sleeve has another shape, such as an oval or a more complex shape, is adjustable, is transparent or any combinations thereof. In various exemplary embodiments, the length of the sleeve is adjustable by varying the location of the outer and inner rings or by gathering or winding portions of the sleeve around the outer ring, the inner ring, an adaptor, another ring or the like and any combination thereof. In various exemplary embodiments, the sleeve is non-adjustable defining a fixed length and diameter access channel. In various exemplary embodiments, the sleeve includes one or more coatings such as a lubricious coating, anti-microbial coating or both. Examples of sealing caps, retractors and/or protectors are described in U.S. Patent Publication No. 2007/0088204 A1, the disclosure of which of incorporated by reference as if set forth in full herein. Examples of a flexible seal or material including gel material are described in U.S. patent application Ser. No. 10/381,220, filed Mar. 20, 2003, the disclosure of which is hereby incorporated by reference as if set forth in full herein.

In various exemplary embodiments, the sealing cap covers the proximal or outer portion of the retractor/protector. In various exemplary embodiments, the sealing cap provides additional access areas or portions. In the illustrated exemplary embodiment, the sealing cap includes a flexible seal or cover made of a flexible material, e.g., gel material, surrounding the sheath and through which robotic manipulators may be inserted directly there through for additional access into the patient. In various exemplary embodiments, auxiliary surgical instruments are insertable directly through the flexible seal in portions around or adjacent the sheath. The flexible seal provides a seal around or sealingly engages an outer surface of the auxiliary surgical instruments as the instruments are inserted, utilized or withdrawn from the flexible seal around the sheath and provides a seal in various exemplary embodiments in the absence of a surgical instrument inserted in the flexible seal around the sheath.

The retractor/protector 820 provides a stable platform to connect the sealing cap 800 to the patient. The stable platform allows movement of the sheath within the flexible seal while minimizing any additional movement or forces caused by movement of the sheath on the flexible seal. As such, the outer portion of the flexible seal, the ring or both reduces or dissociates movement of the flexible seal caused by the sheath relative to the rest of the sealing cap and the patient. Also, the retractor/protector attached to the sealing cap further dissociates movement of the sealing cap on the patient caused by movement of the flexible seal of the sealing cap. The retractor/protector also atraumatically retracts the opening in the patient to increase range of access or mobility of the robotic manipulators and positions the tissue, around and through the opening, away from potential contact or trauma from the inserted surgical robotic manipulators.

In various exemplary embodiments, an instrument shield or retractor shield is disposed between the sealing cap and the retractor to prevent or reduce potential damage to the retractor or protector and/or to direct off-axis manipulators towards the center or opening in the patient. In various exemplary embodiments, the sealing cap may be connected directly to the patient via sutures or adhesive and may be provided with or without the retractor, shield or both.

In various exemplary embodiments, the sheath is removably insertable into the sealing cap and, in various exemplary embodiments, a raised portion of the flexible seal surrounds a cavity to further secure or reinforce the engagement of the sheath with the flexible seal. In various exemplary embodiments, the flexible seal has a uniform height or thickness throughout the seal. In various exemplary embodiments, the flexible seal has a center cavity disposed within the cavity to further assist in the insertion of a manipulator and sealing against the manipulator or in the absence of the manipulator. As such, the center cavity provides another reduced layer of thickness or increased flexibility relative to the surrounding cavity and the surrounding flexible seal, e.g., the material within the cavity or between the cavity and the edge or outer periphery of the sealing cap.

In various exemplary embodiments, the flexible seal within and/or below the sheath provides a seal for a surgical robotic manipulator to be inserted there through or in the absence of a manipulator inserted through the flexible seal. The reduced portion of the flexible seal defined and/or confined by the sheath provides a consistent density or consistency to provide a predefined or pre-known or predictable insertion force that may be used to generate haptic feedback or other similar sensor information to be recognized by the surgical robotics system to identify and/or simulate the insertion and withdrawal of the surgical robotic manipulator.

In various exemplary embodiments, the sealing cap includes a flexible seal being resilient to doming during insufflation and to the insertion and removal of irregularly shaped or sharp robotic manipulators. Anti-doming of the flexible seal of the sealing cap in various exemplary embodiments comprises a mesh or a mesh lined pattern molded into the flexible seal that limits the amount of movement along a central axis of the sealing cap while still providing freedom for the flexible seal to seal around a robotic manipulator. In various exemplary embodiments, as shown for example in FIGS. 17-18, a line 809, e.g., a monofilament line, is cast or molded into the flexible seal in a star or web pattern to reduce doming of the flexible seal during pneumoperitoneum. In various exemplary embodiments, the line is weaved through the apertures or holes in the cap ring 808 to form a pattern to support and/or reinforce the flexible seal under pneumoperitoneum. In various exemplary embodiments, In various exemplary embodiments, the line is weaved into a pattern with the middle of the pattern being clear of the line. In various exemplary embodiments, the ends of the line are tied in a knot and/or adhered and loosely weaved to prevent deformation of cap ring during pre-molding. The anti-doming of the flexible seal prevents or reduces undesired movement of the area of the flexible seal or the sheath within the flexible seal that is sealing around the robotic manipulator and/or the robotic manipulator sealingly engaging the flexible seal. In various exemplary embodiments, the monofilament line is molded into the flexible seal and weaved through apertures in the cap ring in a pattern with the middle of the pattern being clear of the line. In various exemplary embodiments, the monofilament line being made of a material different from the flexible material of the flexible seal and has a thickness smaller than the thickness of the flexible material In various exemplary embodiments, the sealing cap includes a flexible seal fortified to resist puncture or damage from irregularly shaped or sharp robotic manipulators. In various exemplary embodiments, the flexible seal includes one or more shields or protectors, e.g., sheets of puncture resistant film, fabric or the like, within or attached to the flexible seal and/or augmenting a specific access point or area through the flexible seal such as an opening or slit. The one or more shields also help to deflect off-axis robotic manipulators into alignment or towards the center or midline of the patient opening or the flexible seal as the robotic manipulator is inserted or passes through the flexible seal.

In various exemplary embodiments, the one or more shields are embedded in the flexible seal and are arranged inside the inner periphery of the sealing cap. In various exemplary embodiments, the protectors are positioned between the inner and outer surface of the flexible seal. The protectors are confined within a particular area or space of the flexible seal to allow additional access through the surrounding flexible seal as well as to allow freedom of movement of the flexible seal unencumbered or obstructed by the protectors. The flexible seal in one exemplary embodiment is made of a gel material and in various exemplary embodiments an upper surface of the shields and a lower and/or side surfaces of the shields are surrounded by or directly attached and embedded in the flexible seal.

In various exemplary embodiments, as shown for example in FIGS. 15-18, a surgical robotic access system is provided in which a sealing cap includes protectors or shield leaves 801, 803 to protect the flexible seal 804, the robotic sheath, the robotic manipulator or any combination thereof. The shield leaves 801, 803 are embedded in the flexible seal 804 that is attached to or integrated into a ring, cap or cover 808. By embedding the shield leaves in the flexible seal, any forces that may dislodge the shield is eliminated or greatly reduced. In various exemplary embodiments, the shield leaves 801, 803 are a pair of rectangular fabric or film sheets covering a center region of the flexible seal. In various exemplary embodiments, the film or fabric sheets are one by three inch strips. In various exemplary embodiments, the shield leaves have a plurality of openings along their edges or ends assisting in the attachment and securement of the shield leaves to the flexible seal. In various exemplary embodiments, the shield leaves have or define a central opening with the edges of the shield leaves embedded into the flexible seal. In various exemplary embodiments, the shield leaves are made of a material different from the flexible material of the flexible seal and have a higher durometer than the flexible material and/or have a higher leak rate than the flexible material in presence and absence of an instrument inserted therethrough. The shield leaves in various exemplary embodiments are embedded in the flexible seal by attaching to the leaves to a metallic shim. The metallic shim holds the arrangement or placement of the shield leaves to be molded or embedded into the flexible seal. The metallic shim also spaces or separates the leaves to provide a space or opening between the leaves during the molding or embedding of the leaves into the flexible seal. Once formed, the metallic shim can be removed from the flexible seal.

Additionally, a filament or line, as previously described, may also be weaved through the cap ring to form a pattern to further support the flexible seal and the shield and to reduce doming of flexible seal during pneumoperitoneum. As such, the line is cast or molded along with the shield leaves into the flexible seal. In various exemplary embodiments, the leaves are disposed in the middle of the flexible seal to shield an inner layer of a slit, opening or an x-slit within the flexible seal. In various exemplary embodiments, the slit or x-slit is created using sheet metal glued together in a specific orientation providing a taper such that device tips will be funneled towards the center of the slit and protect the flexible seal from puncturing. In various exemplary embodiments, the middle portions of film strips or sheets are glued to x-slit shims to hold the sheets in place while flexible material of the flexible seal is being cured or molded. In various exemplary embodiments, the shield sheets or film has a low friction or non-tacky side to ease manufacturing and operational movement of the shield and a fabric side to provide additional protection to the sheets, the flexible seal, or an opening through the flexible seal or to provide a predefined target area. In various exemplary embodiments, the low friction side is face down in the mold, which faces up proximally or towards a surgeon in operation and the fabric side adheres to the flexible seal and keeps the shield in place in the flexible seal. In various exemplary embodiments, the low friction side is coated or otherwise formed or arranged to remain separate from flexible material of the flexible seal. In various exemplary embodiments, the inserted robotic manipulator or sheath contacts the low friction side of shield and the shield prevents the inserted manipulator or sheath from digging into the flexible material of the flexible seal.

In various exemplary embodiments, the flexible material, e.g., a gel material, is poured into a mold to hold x-slit shim in place and prevent air from being trapped under a sheet. Also, the x-slit shim prevents the shield leaves from resting against the mold as the gel material is being cured to ensure the gel material is between the mold and the shield leaves. As such, the leaves remain within gel material or under the outer surface of the gel material and a hole or opening for the gas (e.g., carbon dioxide) to escape is avoided. After curing, e.g., removing heat and cooling, the x-slit shims are removed while the shield leaves remain within the flexible material. In various exemplary embodiments, the shield leaves are disposed to augment or reinforce the opening or x-slit in the flexible seal.

In various exemplary embodiments, an opening actuator, e.g., one or more handles and lines 811, cord, string or the like are attached to one or more of the shield leaves, e.g., shield leaf 803. Manipulation of the opening actuator opens or closes the shield leaves by adjusting the separation or space between the shield leaves. For example, moving or pulling the line proximally and/or laterally loosens or increases separation, distance or spacing between the shield leaves and/or the portions of the flexible material surrounding or adjacent to the shield to thereby ease placement of robotic manipulator. Similarly, releasing or not manipulating the line allows the shield and/or flexible seal to remain or return to their initial state and thus apply radial or compression force or circumferential pressure and provide sealing engagement with the robotic manipulator or sheath in place or fortify portions of the flexible seal, e.g., around a central opening in the flexible seal.

Figure 19:
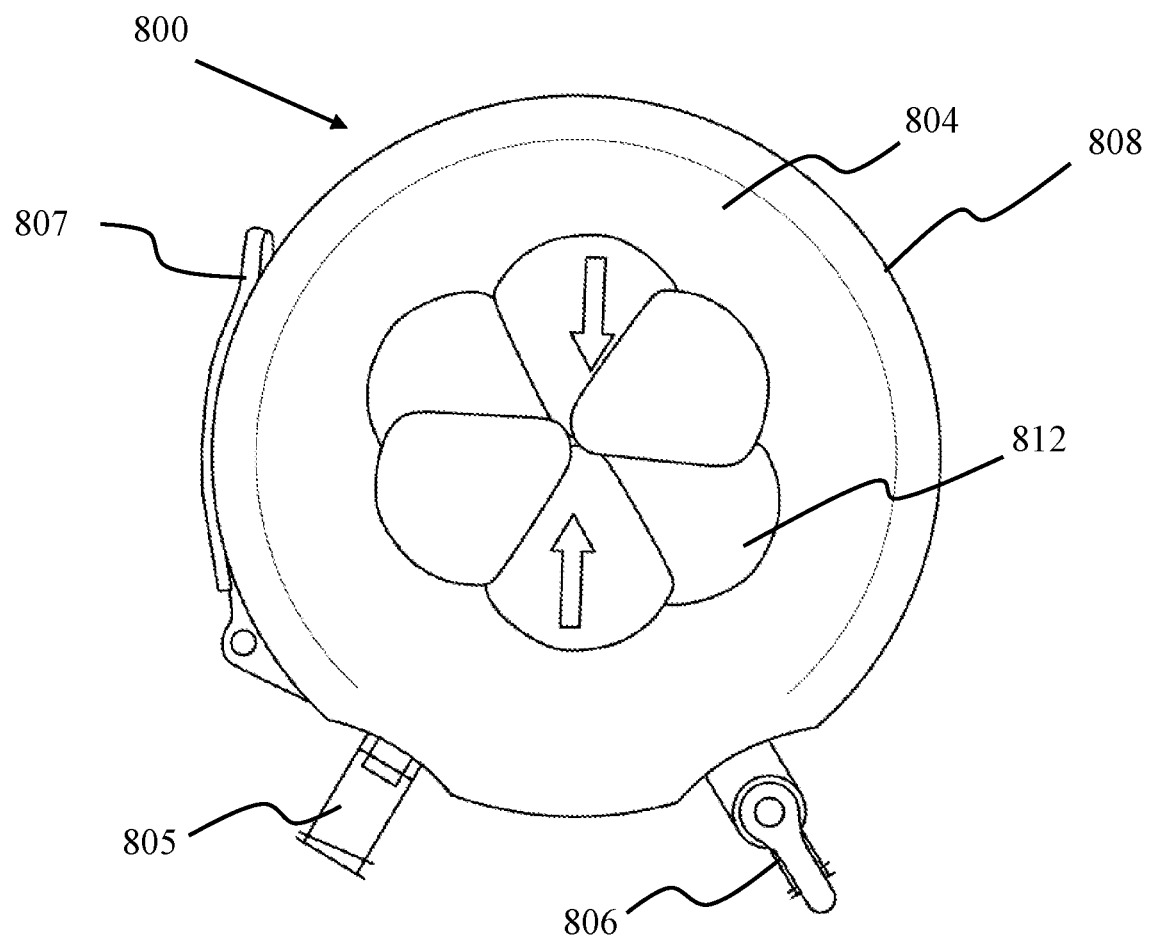
FIG. 19 is a top view of a sealing cap of a surgical robotics access system in accordance with various exemplary embodiments.

In various exemplary embodiments, the shield may be of varied shapes, sizes and number. For example, as shown in FIG. 19, scalloped shields or tear dropped shaped seals 812 are arrayed covering a center region of the flexible seal. The flexible seal surrounding the scalloped shields 812 remains unobstructed. As shown, the shields and/or flexible seal may include indicia or other indicators to highlight a portion of the flexible seal, the shield and/or sealing cap to direct or provide a target area for the sheath and/or robotic manipulator to be inserted therethrough.

In various exemplary embodiments, the scalloped shields so arranged can flex or move distally and assist in moving the flexible seal from the pathway of the inserted sheath or robotic manipulator to guide the sheath or manipulator and partially or fully protect the flexible seal. The scalloped shields are arranged or interconnected with each other such that movement of one of the shields effects movement of the surrounding shields to further guide and facilitate entry of the sheath or robotic manipulators through the flexible seal.

Figure 20:
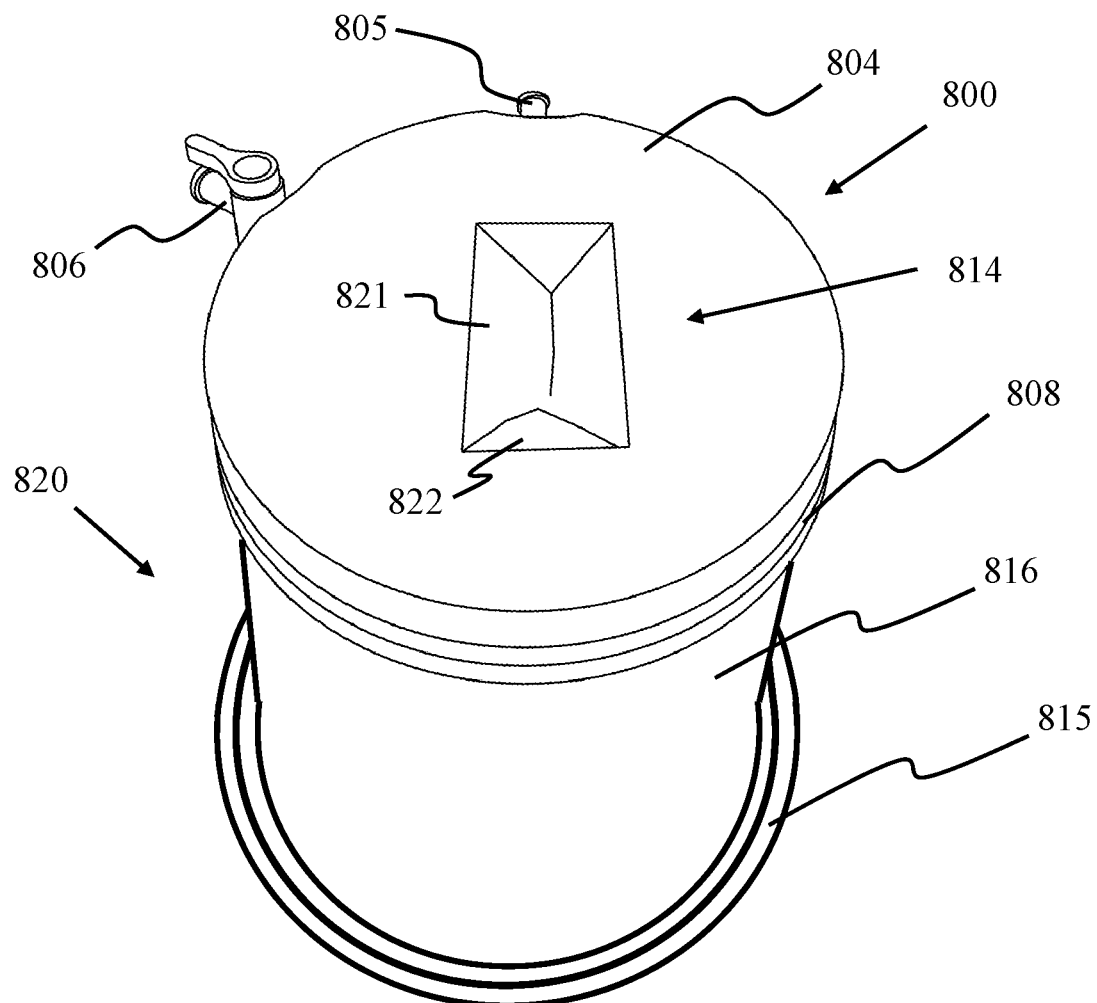
FIG. 20 is a perspective view of a sealing cap and protector of a surgical robotics access system in accordance with various exemplary embodiments.
Figure 21:
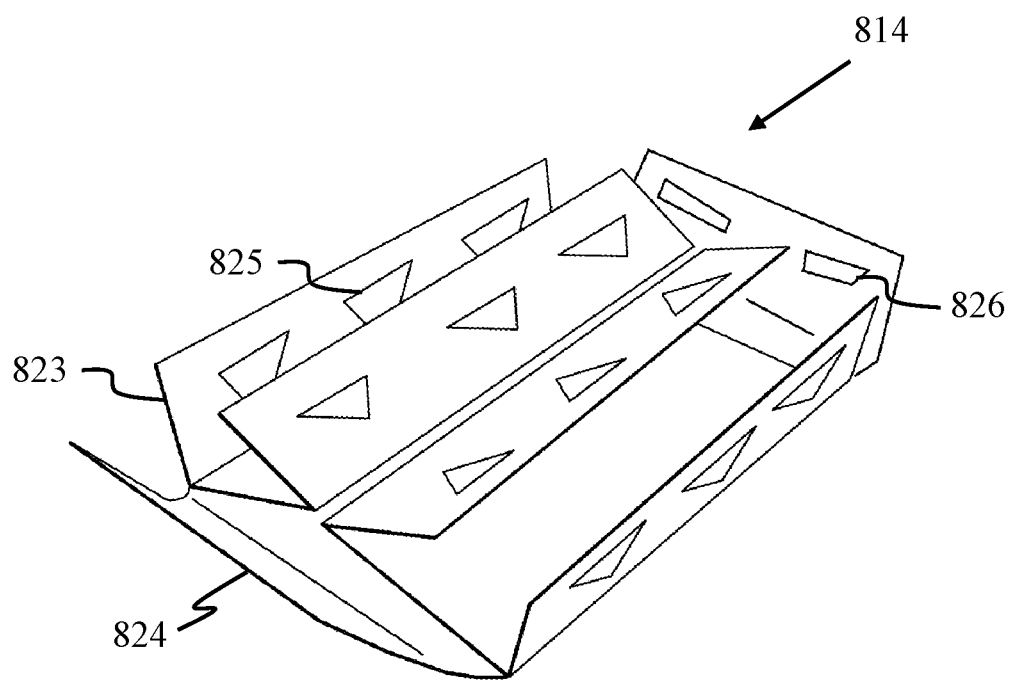
FIG. 21 is a perspective view of a portion of a sealing cap of a surgical robotics access system in accordance with various exemplary embodiments.
Figure 22:
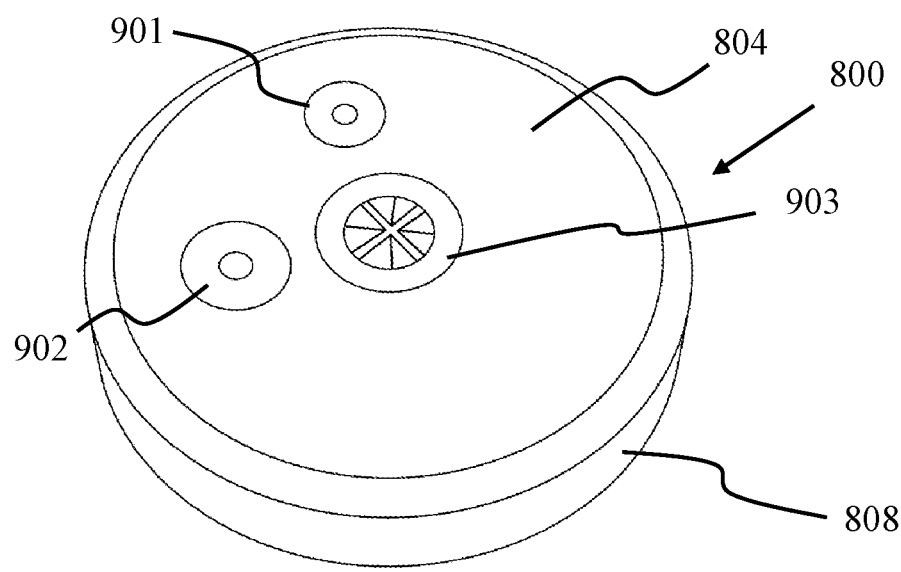
FIG. 22 is a perspective view of a sealing cap of a surgical robotics access system in accordance with various exemplary embodiments.
Figure 23:
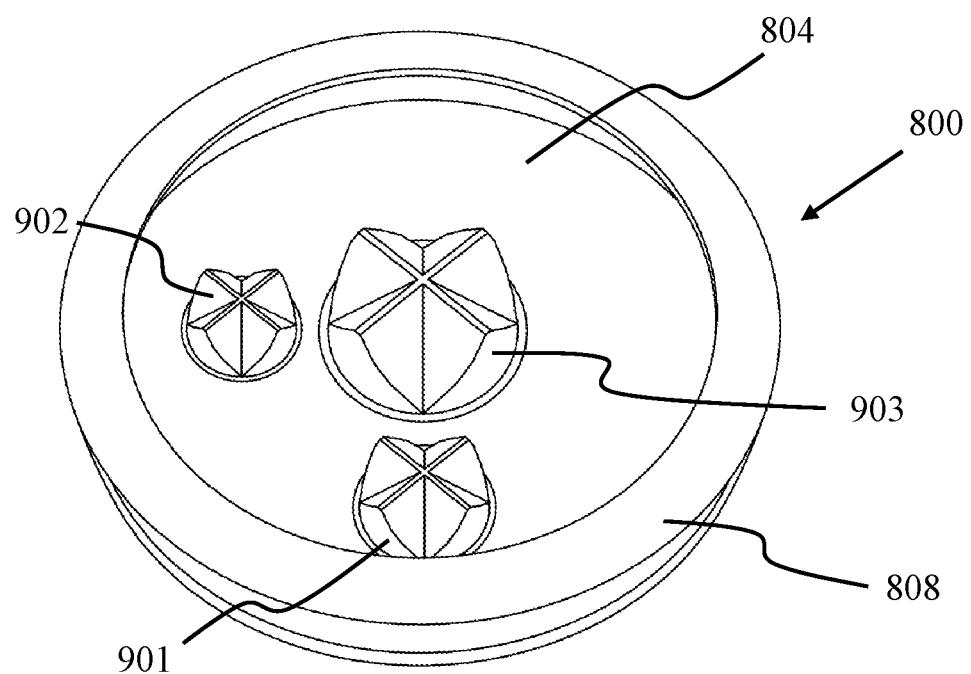
FIG. 23 is a perspective view of a sealing cap of a surgical robotics access system in accordance with various exemplary embodiments.
Figure 24:
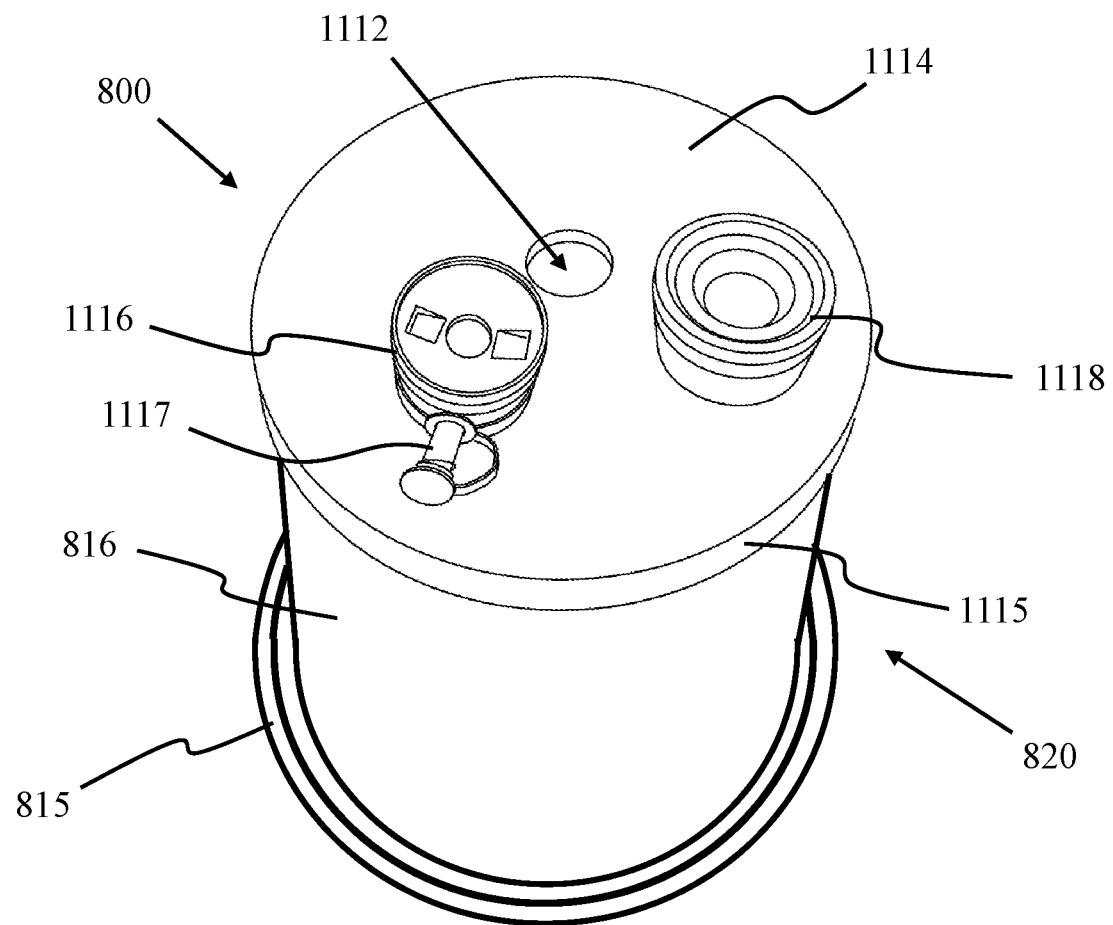
FIG. 24 is a perspective view of a sealing cap and protector of a surgical robotics access system in accordance with various exemplary embodiments.
Figure 25:
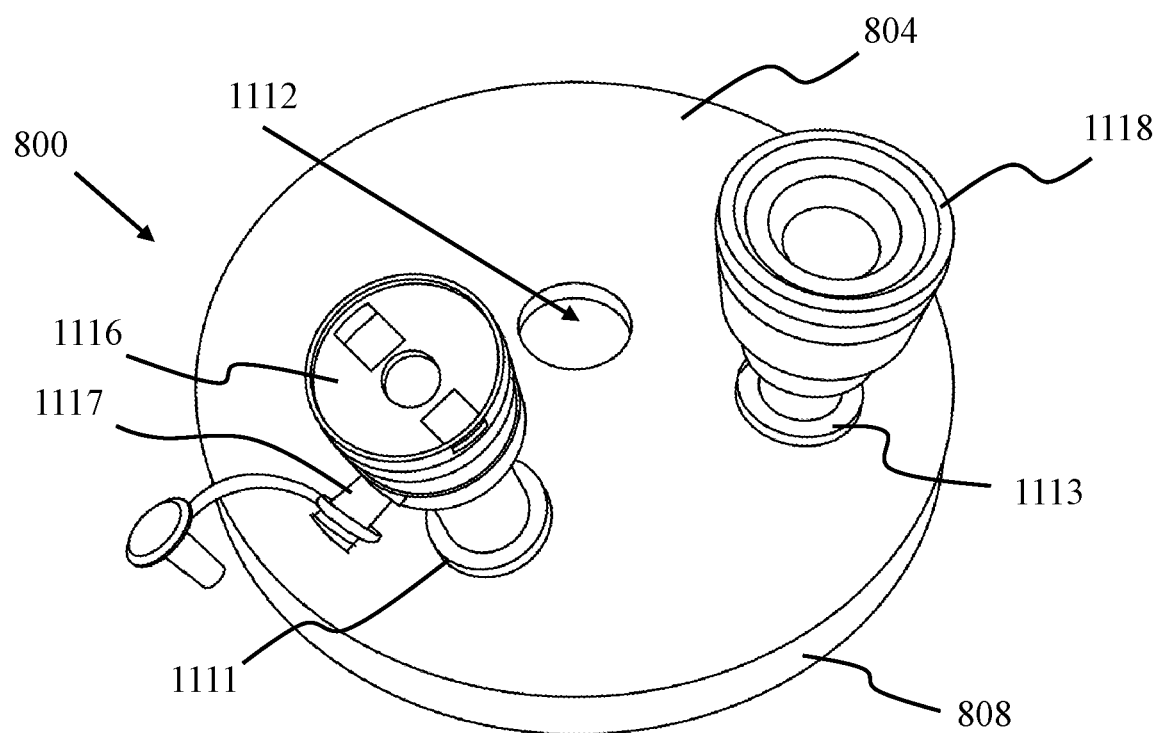
FIG. 25 is a perspective view of a sealing cap of a surgical robotics access system in accordance with various exemplary embodiments.
Figure 26:
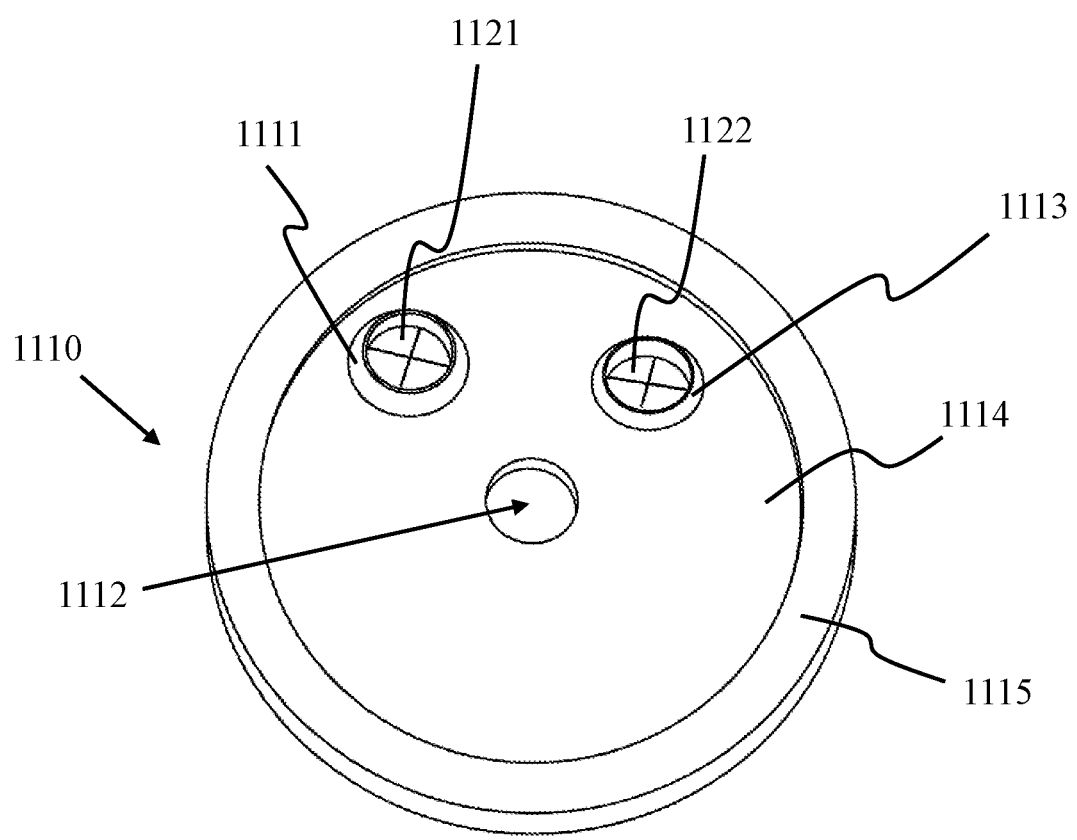
FIG. 26 is a perspective view of a sealing cap of a surgical robotics access system in accordance with various exemplary embodiments.
Figure 27:
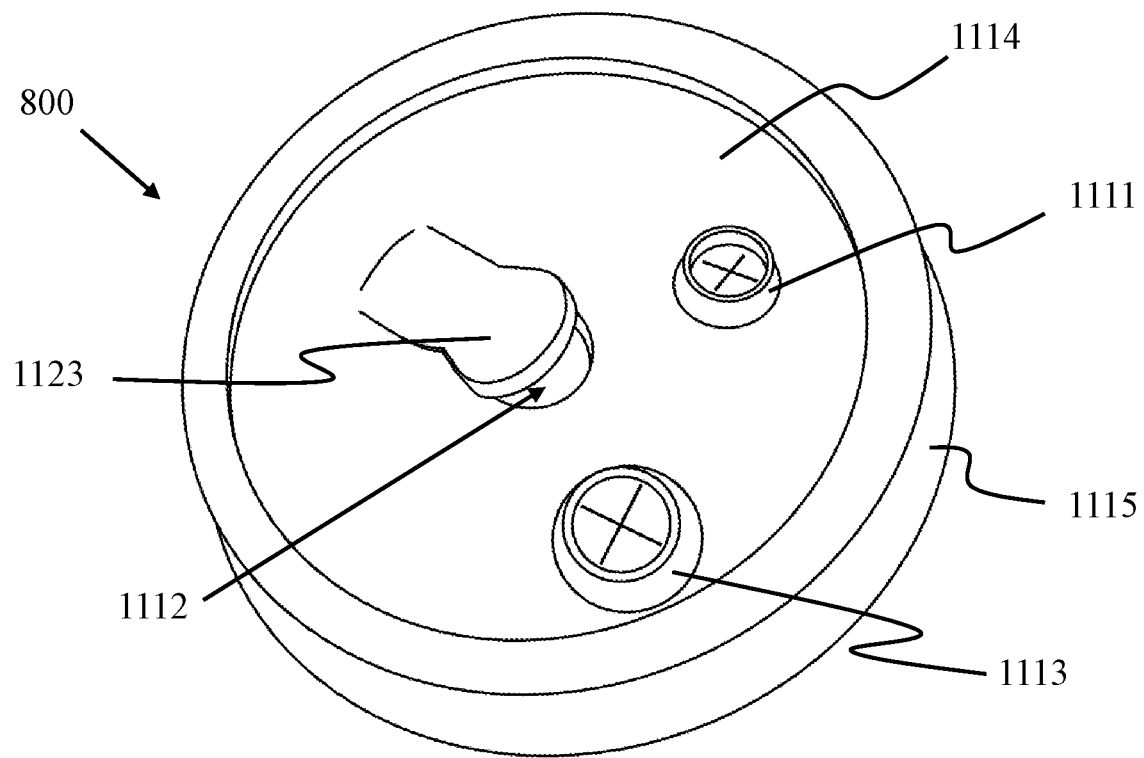
FIG. 27 is a perspective view of a sealing cap of a surgical robotics access system in accordance with various exemplary embodiments.

In various exemplary embodiments, the flexible seal, as shown in FIGS. 20-21, includes a shield 814, e.g., a single piece or monolithic shield, to guide robotic manipulators or sheaths through the access platform and provide further protection for the sheath, flexible seal or access platform. The shield includes holes or apertures along its edges or ends to enhance securement of shield to the flexible seal. In various exemplary embodiments, the shield 814 is a curved or angled plastic or fabric sheet. The shield includes angled side walls 821, each identical and mirror images of each other that meet together at their edge and in various exemplary embodiments over a midline of flexible seal or above the slit. Top and bottom angled walls 822 fill in top or bottom portions of the shield to direct the shield and an inserted sheath or manipulator towards the middle or center edge of the side walls. In various exemplary embodiments, tabs or flanges 823, 824 extend from the side walls, the top wall and/or bottom wall and in various exemplary embodiments include holes or apertures 825, 826 to further fortify, embed or secure attachment of the shield to the flexible seal.

In various exemplary embodiments, the shields or protectors have one edge elevated above an edge at the midline of the flexible seal to provide a tapered or sloped shielded entry to facilitate movement of the protectors and to direct the inserted robotic manipulator towards the slit in the flexible seal. In various exemplary embodiments, the flexible seal or material directly under the protectors are correspondingly shaped and sized to accommodate the shape and size of the protectors. The shields in various exemplary embodiments are cast into the flexible seal to protect or reinforce the flexible seal or material from being torn or punctured by the tips of the surgical robotic manipulators in such a way to effectively disrupt or make ineffective the zero sealing or instrument sealing capabilities of the sealing cap. In various exemplary embodiments, the shields are made out of a soft and durable material to provide a lubricious surface for the tips of the robot manipulators to ride against during insertion or withdrawal of the robot actuators. In various exemplary embodiments, the shield is made from a material different, more durable and rigid or any combination thereof than the material of the flexible seal. In various exemplary embodiments, the shield, shields or protectors are made of a material different from the flexible material of the flexible seal and have a higher durometer than the flexible material and/or have a higher leak rate than the flexible material in presence and absence of an instrument inserted therethrough. In various exemplary embodiments, one or more opening actuators, e.g., one or more handles and/or lines, cord, string or the like, are attached to one or more shields or portions of the shield to adjust, e.g., increase or decrease, the separation or distance between the one or more shields or portions of the shield corresponding with movement of the one or more opening actuators.

In various exemplary embodiments, a double duckbill seal is cast into the flexible seal to provide an additional or separate zero seal or seal in absence of a surgical robotic manipulator. The duckbill seal in various exemplary embodiments is made of a material different from the material of the flexible seal. The duckbill seal is compressible by the surrounding flexible seal to further enhance the seal of the duckbill seal. In various exemplary embodiments, the duckbill seal does not extend through the flexible seal and instead is completely embedded in the flexible seal to further enhance the seal of the sealing cap and the duckbill seal. The protector or shields in various exemplary embodiments may be included and precede the duckbill seal.

In various exemplary embodiments an insufflation port 806, an evacuation port 805 or both are disposed through the ring 808, the flexible seal 804 or both to access the body cavity. As such, gas or fluid such as insufflation gas can be externally supplied via an inlet of the insufflation port 806 from a gas source outside or external to the patient and the robotic access system. The externally supplied gas is introduced into the patient through an outlet of the insufflation port while the flexible seal prevents any gas or fluid from escaping. Similarly, gas or fluid such as smoke may be extracted from within the patient through the inlet of the evacuation port 805 and pulled out externally through an outlet of the evacuation port into an appropriate canister, suction or evacuation system to properly dispose of the potentially harmful or disruptive gas or fluid.

In various exemplary embodiments, an outer portion of the flexible seal is coupled to the ring 808 and in one exemplary embodiment is molded to a plurality of apertures disposed along the periphery of the ring. In various exemplary embodiments, the ring 808 of the sealing cap includes a pivotably coupled latch 807 along with a stationary ledge or flange 810 assisting in removably coupling the sealing cap to the protector. In various exemplary embodiments, the ring and flexible seal are made of the same material and thus together form a monolithic structure. In various exemplary embodiments, as shown for example in FIGS. 22-23, the flexible seal 804 includes one or more zero seals 901, 902, 903 such as a duckbill or flapper seal attached to or integrated into the flexible seal in absence of a trocar, sheath or the like not inserted into the flexible seal. In various exemplary embodiments, one or more septum or instruments seal are integrated or included with one or more zero seal to further sealingly engage with an outer surface of inserted sheath and/or manipulator. The zero seals, instrument seals or both provide additional target areas for the sheaths and/or robotic manipulators and may be provided with reduced thickness or stiffness to ease insertion of an inserted robotic manipulator and sealing of the flexible seal when the robotic manipulator is withdrawn. In various exemplary embodiments, the zero seals 901, 902, 903 and flexible seal 804 are molded as a single monolithic structure and thus are made of the same material.

As shown in FIGS. 24-27, the flexible seal 804 in various exemplary embodiments includes a plurality of apertures. Two of the apertures 1111, 1113 include an elastomeric cylindrical laterally extending bellows that are used to both attach and sealingly engage a trocar or sheath to the flexible seal 804. The surrounding material of the flexible seal 804 is less resilient or stiffer than the bellows surrounding or attached to the apertures of the flexible seal. As such, the surgeon is provided a pronounced degree of movement for the attached trocar or sheath. In various exemplary embodiments, the flexible seal has a central aperture 1112 that is larger than the other apertures. In various exemplary embodiments, each or some of apertures include or have a zero seal such as duckbills 1121, 1122 or flapper seal 1123 attached to or integrated into the respective aperture to provide a seal in absence of a trocar, sheath or the like not inserted into the apertures. In various exemplary embodiments, one or more septum or instruments seals are integrated or included with one or more zero seals to further sealingly engage with an outer surface of an inserted sheath and/or manipulator. In various exemplary embodiments, removable access ports 1116, 1118 of varied diameter size are provided for auxiliary surgical instruments or surgical robotic manipulators and are inserted into the apertures 1111, 1112, 1113 and/or around a sheath or central aperture 1112. In various exemplary embodiments, the removable access ports comprise of a cannula with an attached or integrated seal assembly with an instrument seal, zero seal or both. The cannula in various exemplary embodiments has one or more support structures on the outer surface of the cannula to removably secure the removable access port to the flexible seal. In various exemplary embodiments the removable access ports are all utilized to increase triangulation manipulation or viewing for the surgical procedure and may include additional inlets/outlets for insufflation and/or evacuation.

In various exemplary embodiments, the surgical robotic access system provides access into a patient's body cavity for a 22$mm$ diameter surgical robotic manipulator and/or a sheath. The surgical robotic access system provides a seal, e.g., a zero seal, when the robotic manipulator and/or sheath are not inserted through the robotic access system. The surgical robotic access system also provides an instrument seal when the robotic manipulator is inserted through the robotic access system. The seal prevents the loss or escape of fluids or gases used or encountered in a surgical procedure. The surgical robotic access system in various exemplary embodiments also provides access for introducing or removing of gas or fluids such as insufflation gas, smoke or the like. The surgical robotic access system provides protection for and from distal tips of the robotic manipulator from damaging the surgical robotic access system, the patient and the robotic manipulator.

Figure 28:
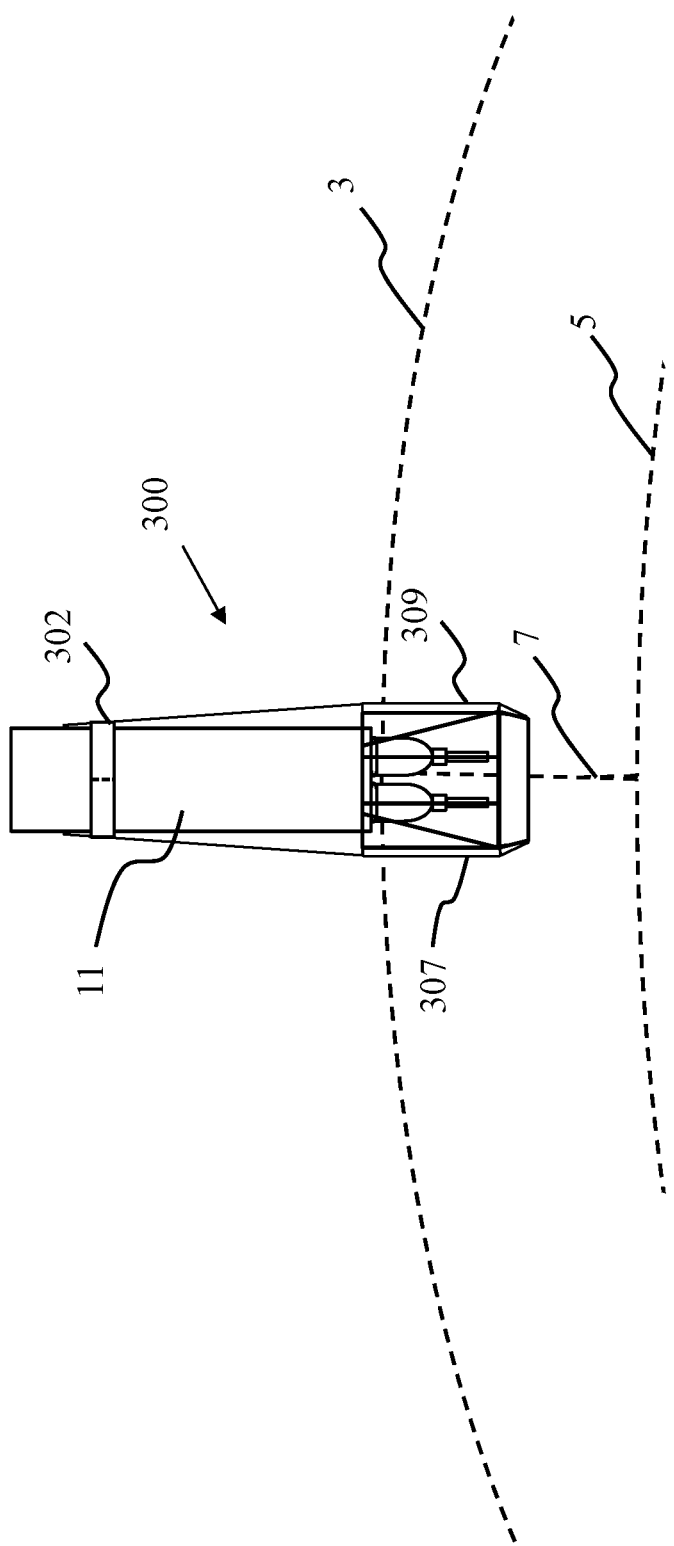
FIG. 28 is a side view of a robotic sheath of a surgical robotics access system in accordance with various exemplary embodiments.
Figure 29:
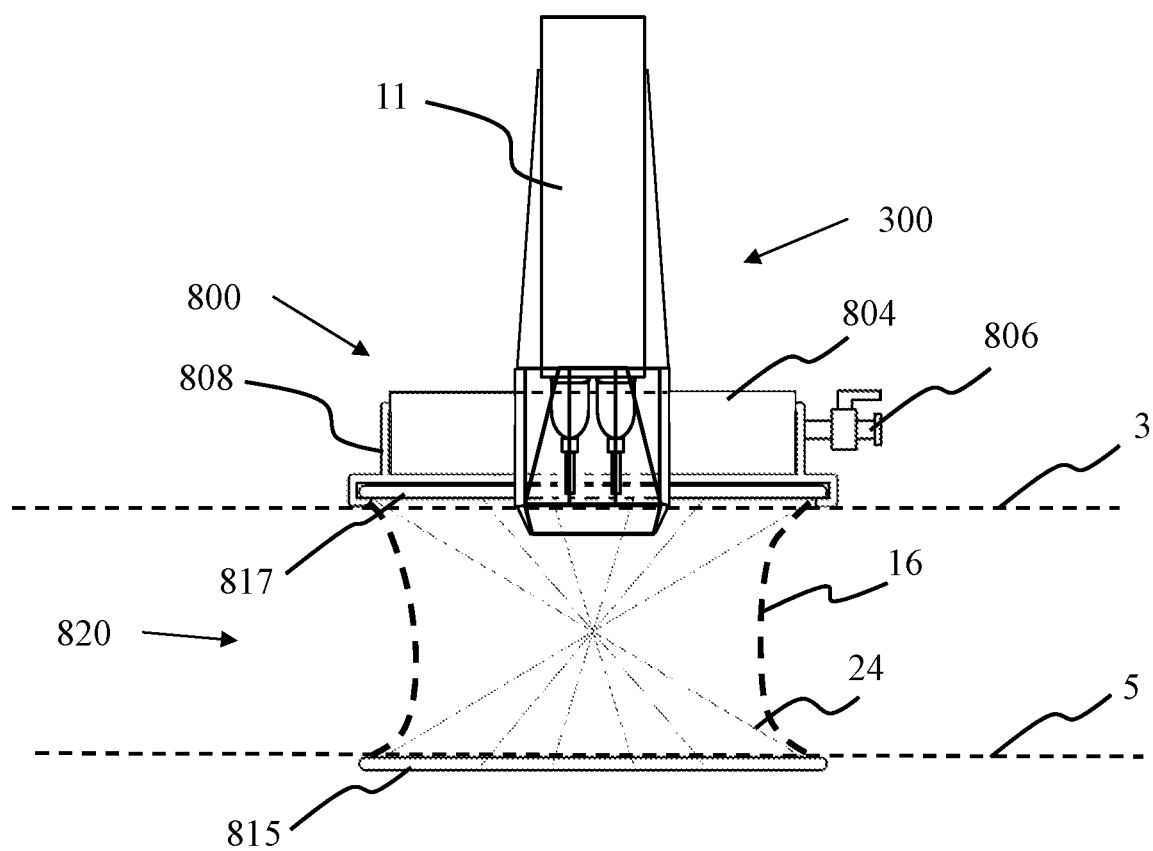
FIG. 29 is a cross-sectional side view of a robotic sheath and sealing cap of a surgical robotics access system in accordance with various exemplary embodiments.
Figure 30:
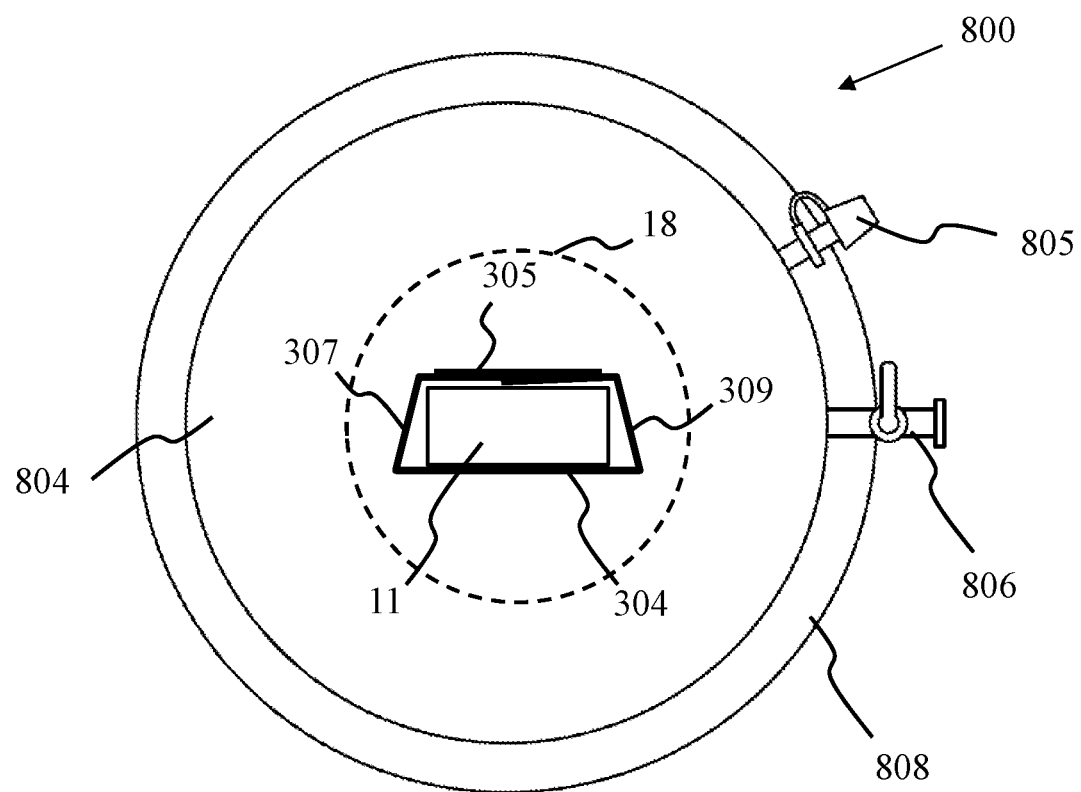
FIG. 30 is a top view of a robotic sheath and sealing cap of a surgical robotics access system in accordance with various exemplary embodiments.

In various exemplary embodiments, a surgical robotic access system provides a seal arrangement for a surgical robotic manipulator to be inserted there through or in the absence of a manipulator. In accordance with various exemplary embodiments, as shown in FIG. 28, the sheath 300 may be introduced through a body wall and into a patient's body cavity through an incision or opening in the patient. Similarly, as shown for example in FIGS. 29-30, the sheath in accordance with various exemplary embodiments may be introduced through an access platform. (Although sheath 300 is shown in FIGS. 28-30, other various sheath exemplary embodiments (e.g., sheaths 100-700) described throughout the application may be similarly used.) Likewise, although a particular surgical access platform and/or sealing cap is shown, other surgical access platform exemplary embodiments and features thereof described throughout the disclosure may be similarly utilized. Prior to introduction into the patient, the sheath has expanded or contracted to accommodate and support the robotic manipulator and otherwise converted an irregularly shaped robotic manipulator to a uniform and smooth form for entry into the patient's body. After insertion into the body cavity via an incision, opening and/or a surgical access platform, the robotic manipulator may be extended distally tearing, unfolding or exiting from the distal end of the sheath to perform its intended surgical function. In various exemplary embodiments, prior to the sheath being introduced into the patient and/or the surgical access platform, the patient's body cavity is not insufflated and after insertion, the patient's body cavity is insufflated. Alternatively or additionally, the sheath may be retracted or pulled back proximally to expose or cause the robotic manipulator to exit the sheath thereby allowing the robotic manipulator to perform its intended surgical function unimpeded. After use, the robotic manipulator may be retracted proximally and/or the sheath may be moved distally to again cover or encase the robotic manipulator within the sheath. As such, the sheath and the robotic manipulator may be removed or withdrawn together from the patient's body and/or surgical site. In various exemplary embodiments, the sheath may be completely removed from the surgical site before or after withdrawal of the robotic manipulator from the patient's body or surgical site. In various exemplary embodiments, a frangible collar 302 is disengaged or torn to detach the sheath from the robotic manipulator.

In accordance with various exemplary embodiments, the dashed lines 24 represent the protector and its film that may be twisted prior to its insertion into or within the opening in the patient. The film twisted can further assist in sealing the opening of the patient. In various exemplary embodiments, the dashed lines 16 represent the body wall and the sleeve of the retractor retracting the opening in the patient to ease access into the patient. In the illustrated exemplary embodiments, one or more of the components are shown transparent or translucent to better show some of the underlying components or features otherwise hidden by the flexible seal or sealing cap. In various exemplary embodiments, the dashed line 18 outlines or provides a different consistency or flexibility of the flexible seal relative to the surrounding material and in various exemplary embodiments the flexible seal within the dashed line 18 is firm or more rigid relative to the surrounding material and thus moves or translates freely relative to the ring while the sheath remains static relative to the flexible seal immediately surrounding the sheath. The dashed lines 3, 5 generally represent the upper and lower surfaces of the body wall of a patient. Additionally, in various exemplary embodiments and operations, the patient's body cavity is insufflated or under pressure. The dashed line 7 represents the mid-line or longitudinal axis of the surgical robotic access system and in various exemplary embodiments represents an initial incision or opening in the patient.

In the illustrated exemplary embodiments, it is exemplified that the surgical robotic access system, e.g., the sealing cap and the sheath, may have different sizes, shapes and dimensions. The dimensions, shapes and sizes may be dictated or determined based on the surgical procedures or the surgical robotic system. The sheath, for example, although shown as generally frustoconical, tubular or cylindrical may be of varied shapes and dimensions such as an hour-glass or the like to optimize the surgical site space or sealing engagement with surgical robotic manipulator or the sealing cap. Similarly, the materials of the surgical robotic access system may vary to optimize the surgical site space or connectivity to the surgical robotic system. In various exemplary embodiments, the sheath is made of a flexible and compressible material or made of a lower durometer than the flexible material to conform to the robotic manipulator to affect an instrument seal due to compressive forces of the body wall or the access platform, e.g., the flexible seal, on the sheath. In various embodiments, the robotic sheath is rigid or is made of a material with a higher durometer than the flexible material of the access platform in that the material of the robotic sheath is arranged to resist compressive forces of the flexible material thereby protecting the surgical robotic manipulator and yet maintaining an insufflation gas seal between the robotic sheath and the flexible material.

Throughout a surgical procedure, the surgical robotic manipulator may be interchanged with other surgical robotic manipulators each having differing or varying geometry and/or dimensions. The robotic manipulator, e.g., exemplary robotic instrument 11, is robotically controlled autonomously or through assistance of a surgeon without a surgeon in direct contact or physically grasping the surgical robotic manipulator. The distal ends of the surgical robotic manipulator in various exemplary embodiments are removable and hot swappable with other distal ends of the surgical robotic manipulator that are arranged to preform specific surgical functions, such as stapling, electro-cautery, grasping, viewing, cutting and the like. In various exemplary embodiments, the robotic manipulator is surrounded by a robotic drape or sleeve integrated with or included with the surgical robotic system but is separate and distinct from the sheath. In various exemplary embodiments, both the robotic sleeve and the robotic manipulators are robotically controlled. The robotic sleeve in various exemplary embodiments includes a flexible robotic housing or tube and collar through which a surgical robotic manipulator can be maneuvered there through and into a patient's body. The robotic sleeve like the surgical robotic manipulator is similarly attached or included with the sheath in accordance with various exemplary embodiments described throughout the application.

The surgical robotic manipulators can vary in shape and sizes and thus the sheath, sealing cap or combinations thereof in various exemplary embodiments provides an adaptable yet static sealing arrangement to seal against the varied shapes and sizes of the surgical robotic manipulators or in the absence of a surgical robotic manipulator. The sheath, sealing cap or combinations thereof also does not damage or disrupt the surgical robotic manipulator. The sheath, sealing cap or combinations thereof also facilitates the seal with the opening in the body and allows freedom of movement of a robotic manipulator which facilitates the seal with or to a robotic sleeve and/or manipulator and reduces potential damage to the robotic sleeve and/or manipulator due to off axis movements. In various exemplary embodiments, the sheath, sealing cap or combinations thereof also facilitates a seal with the opening in the body and the sealing cap allows freedom of movement of a sheath which facilitates the seal with or to a robotic sleeve and/or manipulator and reduces potential damage to a robotic sleeve and/or manipulator due to off axis movements.

The above description is provided to enable any person skilled in the art to make and use the surgical robotic access system described herein and sets forth the best modes contemplated by the inventors of carrying out their inventions. Various modifications, however, will remain apparent to those skilled in the art. It is contemplated that these modifications are within the scope of the present disclosure. Different exemplary embodiments or aspects of such exemplary embodiments may be shown in various figures and described throughout the specification. However, it should be noted that although shown or described separately each exemplary embodiment and aspects thereof may be combined with one or more of the other exemplary embodiments and aspects thereof unless expressly stated otherwise. It is merely for easing readability of the specification that each combination is not expressly set forth. It is therefore also to be understood that the system or devices may be practiced otherwise than specifically described, including various changes in the size, shape and materials. Thus, exemplary embodiments described should be considered in all respects as illustrative and not restrictive.

The invention claimed is:

1. A surgical robotic access system providing instrument access into a patient's body, the surgical robotic access system comprising:
   a surgical robotic access platform having a proximal portion disposed externally to a patient's body and a distal portion positioned within a patient's body, the proximal portion of the surgical robotic access platform including a flexible seal; and
   a robotic sheath having a proximal end and a distal end insertable through the flexible seal of the surgical robotic access platform, the robotic sheath having an expandable cover disposed at the distal end of the robotic sheath and defining a cavity having a proximal opening and a distal opening and through which a surgical robotic manipulator is insertable therethrough;
   wherein the expandable cover comprises a plurality of folds and one or more release lines, wherein the plurality of folds are removably connected to each other via the one or more release lines, and wherein proximal movement of the one or more release lines disengages or separates one or more of the plurality of folds from being connected to each other.

2. The system of claim 1 wherein the expandable cover of the robotic sheath is arranged to encase and surround a distal end of the surgical robotic manipulator within the cavity of the robotic sheath and the flexible seal is arranged to encase and surround the expandable cover of the robotic sheath to compress the expandable cover of the robotic sheath against the distal end of the surgical robotic manipulator and thereby maintain an insufflation gas seal between the robotic sheath and the flexible seal.

3. The system of claim 1 wherein at least one of the one or more release lines are configured to removably connect each of the plurality of folds together, and wherein the proximal movement of the at least one release line causes the plurality of folds to separate from each other thereby allowing at least one of the plurality of folds to unfold distally under pressure of the robotic manipulator being moved distally towards the distal opening of the cavity defined by the expandable cover of the robotic sheath.

4. The system of claim 3 further comprising a perforation in one or more of the plurality of folds, wherein the perforation is located at a connection area where one or more of the plurality of folds is removably connected to the one or more release lines, and wherein the proximal movement of the one or more release lines separates portions of the plurality of folds along the perforation to releasably disengage the release line from the plurality of folds.

5. The system of claim 1 wherein the one or more release lines comprises a first release line that is removably attached to a first subset of the plurality of folds and a second release line that is removably attached to a second subset of the plurality of folds thereby allowing selective movement of one or more of the plurality of folds relative to each other.

6. The system of claim 1 wherein the expandable cover includes an exterior surface and an interior surface, both surfaces being uniform and smooth and wherein the interior surface of the expandable cover is lined with a protective material affixed to the interior surface, the protective material being a material different from a material of the expandable cover and having a lower durometer than the material of the expandable cover.

7. The system of claim 1 wherein the flexible seal further comprises a shield, the shield located at a center of the flexible seal and embedded within the flexible seal, wherein the shield has a plurality of openings along an edge of the shield embedded within the flexible seal, the shield being made of a material that is:
   different from a flexible material of the flexible seal,
   has a higher durometer than the flexible material of the flexible seal, and
   has a higher leak rate than the flexible material of the flexible seal in presence and absence of an instrument inserted therethrough.

8. The system of claim 7 further comprising one or more actuators attached to at least one shield portion of the shield to adjust a distance between two or more shield portions with movement of at least one of the one or more actuators.

9. The system of claim 1 wherein the cavity of the expandable cover of the robotic sheath is arranged to expand upon insertion of the surgical robotic manipulator into the cavity and the flexible seal is arranged to encase and surround the expandable cover of the robotic sheath, the robotic sheath being made of a material with a lower durometer than the surgical robotic manipulator and being arranged to conform to the surgical robotic manipulator due to compressive forces of the flexible seal of the surgical robotic access platform arranged to compress the cavity of the expandable cover of the robotic sheath against the distal end of the surgical robotic manipulator and to maintain an insufflation gas seal between the surgical robotic manipulator, the robotic sheath and the flexible seal and wherein a distal most end of the robotic sheath is operationally disposed beneath a lower surface of the flexible seal and the proximal portion of the robotic sheath and the flexible seal are operationally disposed outside of the patient's body, the proximal portion of the robotic sheath having a retrieval tail proximally extending from the expandable cover of the robotic sheath and the robotic sheath being removable from the surgical robotic manipulator with a distal portion of the surgical robotic manipulator being disposed through the flexible seal of the surgical access platform.

10. The system of claim 1, wherein the plurality of folds comprises a first fold and a second fold that are configured to cover sides of the surgical robotic manipulator inserted within the robotic sheath.

11. The system of claim 1, wherein the plurality of folds comprises a middle fold configured to cover the distal end of the robotic sheath.

12. The system of claim 7, wherein the shield of the flexible seal comprises a plurality of portions that are identical and mirror images with respect to each other, and wherein a pair of shield portions of the plurality of portions meet together at their respective edge over a midline of the flexible seal.

13. The system of claim 7, wherein the shield of the flexible seal comprises one or more shield portions that have an elevated edge above a midline of the flexible seal to provide a tapered or sloped shielded entry that facilitates movement of the surgical robotic manipulator towards a middle of the flexible seal.

14. The system of claim 7, wherein the shield further comprises holes or apertures that further fortify, embed, or secure the shield to the flexible seal.

15. The system of claim 7, wherein the shield of the flexible seal comprises a lubricious surface to facilitate insertion or withdrawal of the surgical robotic manipulator through the flexible seal.

16. The system of claim 8, wherein the one or more actuators used to adjust the distance between the two or more shield portions comprise one or more of handles, lines, cords, or strings.

17. The system of claim 1, wherein:
the plurality of folds comprises a first fold and a second fold configured to cover sides of the surgical robotic manipulator and a third fold configured to cover the distal end of the robotic sheath, and
at least one release line of the one or more release lines removably connects the third fold to both the first fold and the second fold, and wherein the proximal movement of the one release line disengages or separates the third fold from both the first fold and the second fold while the first and second folds remain connected.

18. The system of claim 17, wherein additional movement of the at least one release line, after the third fold has been disengaged or separated from the first fold and the second fold, is configured to regulate movement of the third fold with respect to the distal opening of the cavity defined by the expandable cover of the robotic sheath.

19. The system of claim 1, wherein
the plurality of folds comprises a first fold and a second fold configured to cover sides of the surgical robotic manipulator and a third fold configured to cover the distal end of the robotic sheath, and
at least one release line of the one or more release lines removably connects the first, second and third folds together, and wherein the proximal movement of the one release line disengages or separates each of the first, second, and third fold from each other.

20. A robotic sheath comprising:
a proximal end;
a distal end; and
an expandable cover,
wherein the expandable cover is disposed at the distal end and defines a cavity having a proximal opening and a distal opening through which a surgical robotic manipulator is insertable therethrough,
wherein the expandable cover comprises a plurality of folds and one or more release lines, wherein the plurality of folds are removably connected to each other via the one or more release lines, and wherein movement of the one or more release lines is configured to disengage or separate one or more of the plurality of folds from other folds.

* * * * *